United States Patent [19]

Tatton et al.

[11] Patent Number: 5,767,164
[45] Date of Patent: Jun. 16, 1998

[54] USE OF DEPRENYL TO RESCUE DAMAGED NERVE CELLS

[75] Inventors: William G. Tatton; Carol E. Greenwood, both of Toronto, Canada

[73] Assignee: Innovations Foundation, Toronto, Canada

[21] Appl. No.: 374,332

[22] Filed: Jan. 18, 1995

Related U.S. Application Data

[63] Continuation of Ser. No. 203,726, Feb. 28, 1994, Pat. No. 5,444,095, which is a continuation of Ser. No. 929,579, Aug. 14, 1992, abandoned, which is a continuation-in-part of Ser. No. 772,919, Oct. 8, 1991, abandoned, which is a continuation-in-part of Ser. No. 678,873, Apr. 4, 1991, abandoned.

[51] Int. Cl.$^6$ .................................................. A61K 31/135
[52] U.S. Cl. ......................................................... 514/654
[58] Field of Search ............................................. 514/654

[56] References Cited

U.S. PATENT DOCUMENTS

| | | | |
|---|---|---|---|
| 4,861,800 | 8/1989 | Buyske | 514/646 |
| 4,960,797 | 10/1990 | Ecsery | 514/654 |

FOREIGN PATENT DOCUMENTS

| | | | |
|---|---|---|---|
| 0 473 252 A2 | 3/1991 | European Pat. Off. | 31/135 |
| WO 88/04552 | 6/1988 | WIPO | 31/135 |
| WO 90/01928 | 3/1990 | WIPO | 31/135 |

OTHER PUBLICATIONS

Merck Index, 10th edition #52876, 6902, 1983.
CA 106:168235, Youdin et al 1987.
Medline 89036757, Fuller et al, 1988.
Birkmayer, W. et al.; (1985) "Increased Life Expectancy Resulting from Addition of L–Deprenyl to Madopar® Treatment in Parkinson's Disease: A Longterm Study", *J. Neural Transmission;* 64; pp. 113–127.
Finnegan, Kevin T. et al.; (1990) "Protection against DSP–4–induced neurotoxicity by deprenyl is not related to its inhibitioin of MAO B", *Euro. J. Pharmacol.;* 184(1); abstract of pp. 119–126.
Greenwood, Carol E. et al.; (1991) "Increased Dopamine Synthesis in Aging Substantia Nigra Neurons"; *Neurobiology of Aging;* vol. 12; pp. 557–565.
Jonakait, G. Miller et al.; (1988) "Development of serotonin, substance P and thyrotrophin–releasing hormone in mouse medullary raphe grown in organotypic tissue culture: developmental regulation by serotonin"; *Brain Research*, 473; pp. 336–343.
Juorio, A.V. et al.; (1991) "Electrical Stimulation of the Substantia Nigra and Changes of 2–Phenylethylamine Synthesis in the Rat Striatum"; *Journal of Neurochemistry;* 56; pp. 213–220.
Matsui, Yoshiki and Kumagae, Yoshihiro; (1991) "Monoamine oxidase inhibitors prevent striatal neuronal necrosis induced by transient forebrain ischemia"; *Neuroscience Letters;* 126; pp. 175–178.
The Merck Index; (1983) 10th edition, Windholz, M. (Ed.), abstract 2893, p. 423, abstract 6988, p. 1023, abstract 1983; p. 282.

Rinne; (1991) "Nigral degeneration in Parkinson's disease in relation to clinical features"; *Acta Neurol Scand.;* 84: Supp. 136; pp. 87–90.
Rinne et al.; (1991) "Selegine (deprenyl) treatment and death of nigral neurons in Parkinson's disease"; *Neurology;* 41; pp. 859–861.
Seniuk et al; (1990); "Dose–dependent destruction of the coeruleus–cortical and nigral–striatal projections by MPTP"; *Brain Res.;* 527(1); pp. 7–20.
Tatton et al.; (1992); "Interactions Between MPTP–Induced and Age–Related Neuronal Death in a Murine Model of Parkinson's Disease"; *Can. J. Neurological Sciences;* 19(1) (Supp.); pp. 124–133.
Tatton, W.G and Greenwood, C.E.; (1991); "Rescue of Dying Neurons: A New Action for Deprenyl in MPTP Parkinsonism"; *Journal of Neuroscience Research;* 30; pp. 666–672.
Tatton et al.; (1991) "Different Rates of Age–Related Loss For Four Murine Monaminergic Neuronal Populations"; *Neurobiol. of Aging;* 12; pp. 543–556.
Tatton et al; (1991) "Transmitter synthesis increases in substantia nigra neurons of the aged mouse"; *Neuroscience Letters;* 131; pp. 179–182.
Tatton et al; (1990); "MPTP produces reversible disappearance of tyrosine hydroxylase–containing retinal amacrine cells"; *Brain Res.;* 527(1); pp. 21–31.
Timar, Julia; (1989) "Recovery of Mao–B Enzyme Activity After (–)Deprenyl (Selegiline) Pretreatment, Measured in Vivo"; *Acta Physiologica Hungarica;* vol. 74(3–4); pp. 259–266.
Torok, Tamas L. et al; (1987) "Transmitter releasing action of selegiline ((–)–deprenyl) from peripheral sympathetic nerves under different experimental conditions"; *J. Pharm. Pharmacol.;* 39(10); abstract of pp. 797–802, p. 48 of Chemical Abstracts.
Zsilla, Gabriella et al.; (1984) "Neurochemical evidences for facilitation of dopaminergic function in rat brain by repeated doses of (–) deprenyl"; *Dev. Neurosci.* (Amsterdam); 17 *(Regular Transm. Funct.: Basic Clin. Aspects);* abstract of pp. 345–348; p. 64 of Chemical Abstracts.
Zsilla, Gabriella et al.; (1986) "The Effect of Repeated Doses of (–) Deprenyl On The Dynamics of Monoaminergic Transmission. Comparison With Clorgyline"; *Pol. J. Pharmacol. Pharm.;* 38; pp. 57–67.
Zsilla, Gabriella et al.; (1983) "(–)–Deprenyl A Selective Mao 'B' Inhibitor Increases [$^3$H]imipramine Binding and Decreases β–Adrenergic Receptor Function", *European Journal of Pharmacology;* 89; pp. 111–117.
Zsilla, G. and Knoll, J.; (1982) "The Action of (–)Deprenyl on Monamine Turnover Rate in Rat Brain"; *Typical and Atypical Antidepressants: Molecular Mechanisms;* pp. 211–217.

*Primary Examiner*—Rebecca Cook
*Attorney, Agent, or Firm*—Elizabeth A. Hanley; Mark D. Russett; Lahive & Cockfield, LLP

[57] ABSTRACT

The present invention relates to the use of deprenyl or derivatives or analogues of deprenyl to rescue damaged nerve cells in an animal; to pharmaceutical compositions containing deprenyl adapted for such use; and, to methods for the treatment of disorders of the nervous system by rescuing damaged nerve cells.

17 Claims, 33 Drawing Sheets

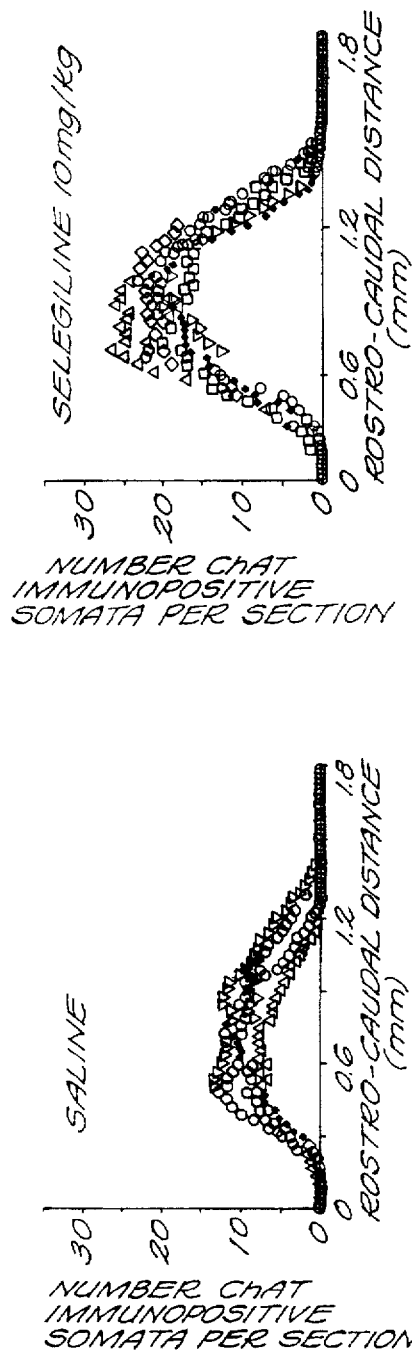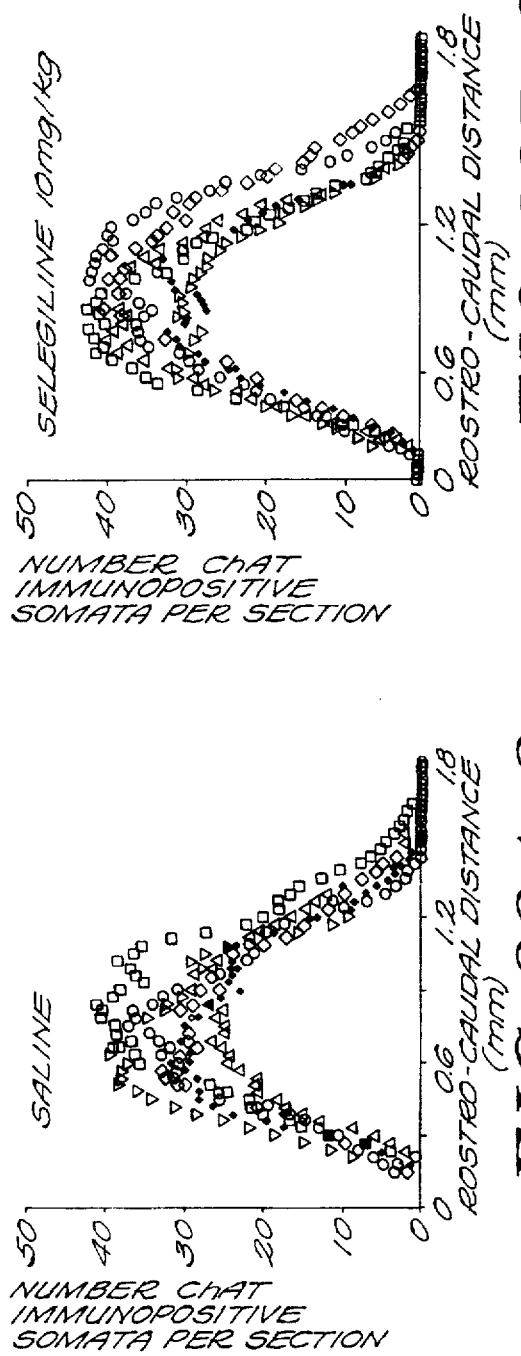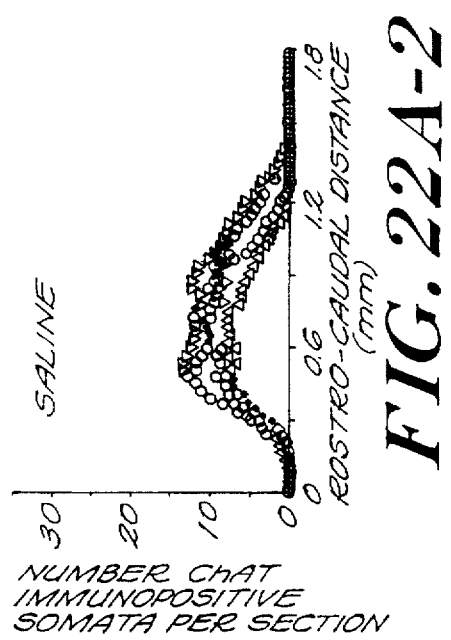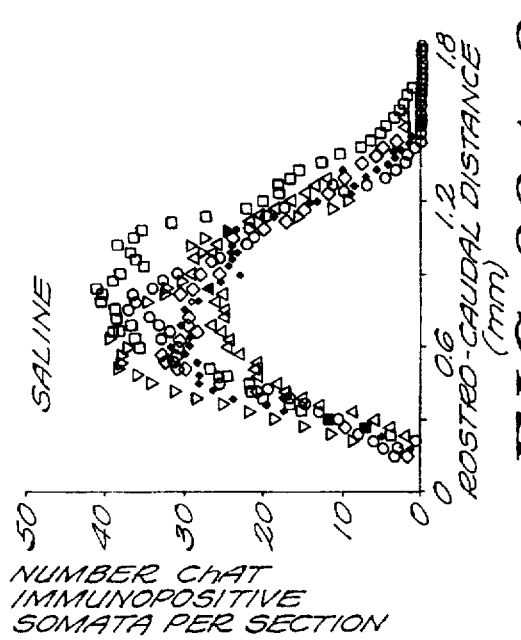

USE OF DEPRENYL TO RESCUE DAMAGED NERVE CELLS

This application is a continuation of application Ser. No. 08/203,726 filed on Feb. 28, 1994, now U.S. Pat. No. 5,444,095, which in turn is a continuation application of Ser. No. 07/929,579, filed on Aug. 14, 1992, abandoned, which in turn is a continuation-in-part of Ser. No. 07/772,919 filed on Oct. 8, 1991 (now abandoned), which is a continuation-in-part of Ser. No. 07/678,873 filed on Apr. 4, 1991 (now abandoned), the contents of all of the aforementioned applications are expressly incorporated by reference.

FIELD OF THE INVENTION

The present invention relates to the use of deprenyl or derivatives or analogues of deprenyl to rescue damaged nerve cells in an animal; to pharmaceutical compositions containing deprenyl adapted for such use; and, to methods for the treatment of disorders of the nervous system by rescuing damaged nerve cells in an animal. The invention also relates to methods for testing drugs for their activity in rescuing nerve cells in an animal.

BACKGROUND OF THE INVENTION

Deprenyl (also referred to herein as selegiline or R-(−)-N,α-Dimethyl-N-2-propynyl phenethylamine) was first used as an adjunct to conventional drug therapy (L-dihydroxyphenylalanine (L-DOPA) plus a peripheral decarboxylase inhibitor) of Parkinson's disease (PD) in Europe over a decade ago on the basis that as a selective monoamine oxidase-B (MAO-B) inhibitor, it would elevate brain dopamine levels and potentiate the pharmacologic action of dopamine formed from L-DOPA, and yet prevent the tyramine-pressor effect observed with non-selective MAO inhibitors. The combined drug therapy was reported to prolong the anti-akinetic effects of L-DOPA, resulting in the disappearance of on-off effects, reduced functional disability, and increased life-expectancy in PD patients (Bernheimer, H., et al., J. Neurolog. Sci., 1973. 20: p. 415–455, Birkmayer, W., et al., J. Neural Transm., 1975. 36: p. 303–336, Birkmayer, W., et al., Mod. Prob. Pharmacopsychiatr., 1983. 19: p. 170–177, Birkmayer, W. and P. Riederer, Hassler, R. G. and J. F. Christ (Ed.) Advances In Neurology. 1984. 40(Y): p.0–89004, and Birkmayer, W., et al., J. Neural Transm., 1985. 64(2): p. 113–128).

Studies examining deprenyl as an adjunct to conventional L-DOPA therapy have reported a short term benefit which was usually lost by 1 year or less. Some, but not all, have reported that the levodopa dose can be decreased when taken in conjunction with deprenyl (Elizan, T. S., et al., Arch Neurol, 1989. 46(12): p. 1280–1283, Fischer, P. A. and H. Baas, J. Neural Transm. (suppl.), 1987. 25: p. 137–147, Golbe, L. I., Neurology, 1989. 39: p. 1109–1111, Lieberman, A. N. et al., N.Y. State J. Med., 1987. 87: p. 646–649, Poewe, W., F. Gerstenbrand, and G. Ransomayr, J. Neural Transm. (suppl.), 1987. 25: p. 137–147, Cedarbaum, J. M., M. Hoey, and F. H. McDowell, J. Neurol Neurosurg Psychiatry, 1989. 52(2): p. 207–212, and Golbe, L. I., J. W. Langston, and I. Shoulson, Drugs, 1990. 39(5): p. 646–651).

Increasingly deprenyl is being administered to Parkinson's disease patients following reports (Parkinson, S. G. Arch Neurol 46, 1052–1060 (1989) and U.S.A., P. S. G. N. Engl. J. Med. 321, 1364–1371 (1989)) that it delays the disease's progression; however, no satisfactory mechanism has been proposed to explain its action.

Support for the use of deprenyl in Parkinson's disease (PD) is largely based on the findings of the DATATOP project (Parkinson, S. G. Arch Neurol 46, 1052–1060 (1989) and U.S.A., P. S. G. N. Engl. J. Med. 321, 1364–1371 (1989)). This multicentre study reported that deprenyl delays the onset of disabling symptoms requiring additional pharmacotherapy by nearly one year; these findings were reproduced in an independent but smaller study (Tetrud, J. W. & Langston, J. W. Science 245, 519–522 (1989)). Unfortunately, the design of the DATATOP study and its conclusions have come under strong criticism (Landau, W. M. Neurology 40, 1337–1339 (1990). Furthermore, while the authors of these projects state that their results are consistent with the hypothesis that deprenyl slows the progression of PD (Parkinson, S. G. Arch Neurol 46, 1052–1060 (1989), U.S.A., P. S. G. N. Engl. J. Med. 321, 1364–1371 (1989) and Tetrud, J. W. & Langston, J. W. Science 249, 303–304 (1990)), "they by no means constitute proof" (Tetrud, J. W. & Langston, J. W. Science 249, 303–304 (1990)).

It has been proposed that deprenyl, an MAO-B inhibitor, may delay the progression of PD by minimizing free-radical induced death of surviving dopaminergic nigrostriatal (DNS) neurons (Langston, J. W. in Parkinson's Disease and Movement Disorders (eds. Jankovic, J. & Tolosa, E.) 75–85 (Urban and Schwarzenberg, Baltimore-Munich 1988)) based on the observation that deprenyl could block MPTP-induced neurotoxicity in primates (Langston, J. W., Forno, L. S. Robert, C. S. & Irwin, I. Brain Res 292, 390–394 (1984)) and the hypothesis that other environmental toxins with mechanisms of action similar to that of MPTP may be involved in the etiology of PD (Tanner, C. M. TINS 12, 49–54 (1989)). However, since MAO-B is not present in dopaminergic neurons (Vincent, S. R. Neuroscience 28, 189–199 (1989), Pintari, J. E., et al. Brain Res 276, 127–140 (1983), Westlund, K. N., Denney, R. M., Kochersperger, L. M., Rose, R. M. & Abell, C. W. Science (Wash D.C.) 230, 181–183 (1985) and Westlund, K. N., Denney, R. M., Rose, R. M. & Abell, C. W. Neuroscience 25, 439–456 (1988)), it is unclear how its inhibition would protect DNS neurons unless another highly toxic compound were formed in non-dopaminergic neurons which could in turn damage DNS neurons in a manner analogous to that of MPTP. Surprisingly, no investigation has included the measurement of DNS neuronal numbers to determine whether deprenyl could influence neuronal survival when measured after MPTP has been cleared from the central nervous system.

SUMMARY OF THE INVENTION

Broadly stated the present invention relates to the use of deprenyl or a derivative of deprenyl, or an analogue of deprenyl to rescue damaged nerve cells in a patient.

The invention also relates to a pharmaceutical composition for use in the treatment of disorders of the nervous system comprising an amount of deprenyl, a derivative of deprenyl, or an analogue of deprenyl, effective to rescue damaged nerve cells in a patient.

The invention further relates to a method for the treatment of disorders of the nervous system by rescuing damaged nerve cells in a patient comprising administering to a patient an amount of deprenyl, a derivative of deprenyl, or an analogue of deprenyl, effective to rescue damaged nerve cells.

The invention also relates to methods for testing a drug for activity in rescuing damaged nerve cells.

The terms "rescue of damaged nerve cells" or "rescuing of damaged nerve cells" herein refers to the reversal of the sequence of damage to death in lethally damaged nerve cells and/or compensation in part for the loss of muscle-derived trophic support.

In accordance with one embodiment of the invention a method for testing a drug for activity in rescuing nerve cells comprising administering an agent having neurotoxic activity to a test animal; administering the drug to the test animal; sacrificing the test animal within a period of 20 days from completion of administration of the agent; taking serial sections of the brain through the substantia nigra compacta; determining the number of tyrosine hydroxlyase positive somata in alternate serial sections of the brain through the substantia nigra compacta and determining the number of Nissl stained positive substantia nigra compacta in intervening serial sections; and comparing the number of tyrosine hydroxlyase positive somata and Nissl stained somata determined with the number of tyrosine hydroxlyase positive somata and Nissl stained somata in serial sections of the brain through the substantia nigra compacta of a control animal which has not been administered the drug.

In accordance with another embodiment of the invention a method for testing a drug for activity in rescuing damaged nerve cells in a patient is provided comprising carrying out an axotomy on a test animal; administering the drug to the test animal; determining the number of choline acetyl transferase positive somata for histological sections from the site of the axotomy; and comparing the number of choline acetyl transferase positive somata determined with a number of choline acetyl transferase positive somata in serial sections from the site of the axotomy in a control animal which has not been administered the drug.

BRIEF DESCRIPTION OF THE DRAWINGS

Further details of the invention are described below with the help of the examples illustrated in the accompanying drawings in which:

FIG. 19 shows photomicrographs of adjacent ChAT immunoreacted (A1 and B1) and Nissl stained (A2 and B2) sections through the facial nucleus ipsilateral to transection of the facial nerve;

FIG. 22 shows ChAT+ counts for facial motoneurons in 35 day old rats after a unilateral axotomy at 14 days of age;

DETAILED DESCRIPTION OF THE INVENTION

Figure 1:
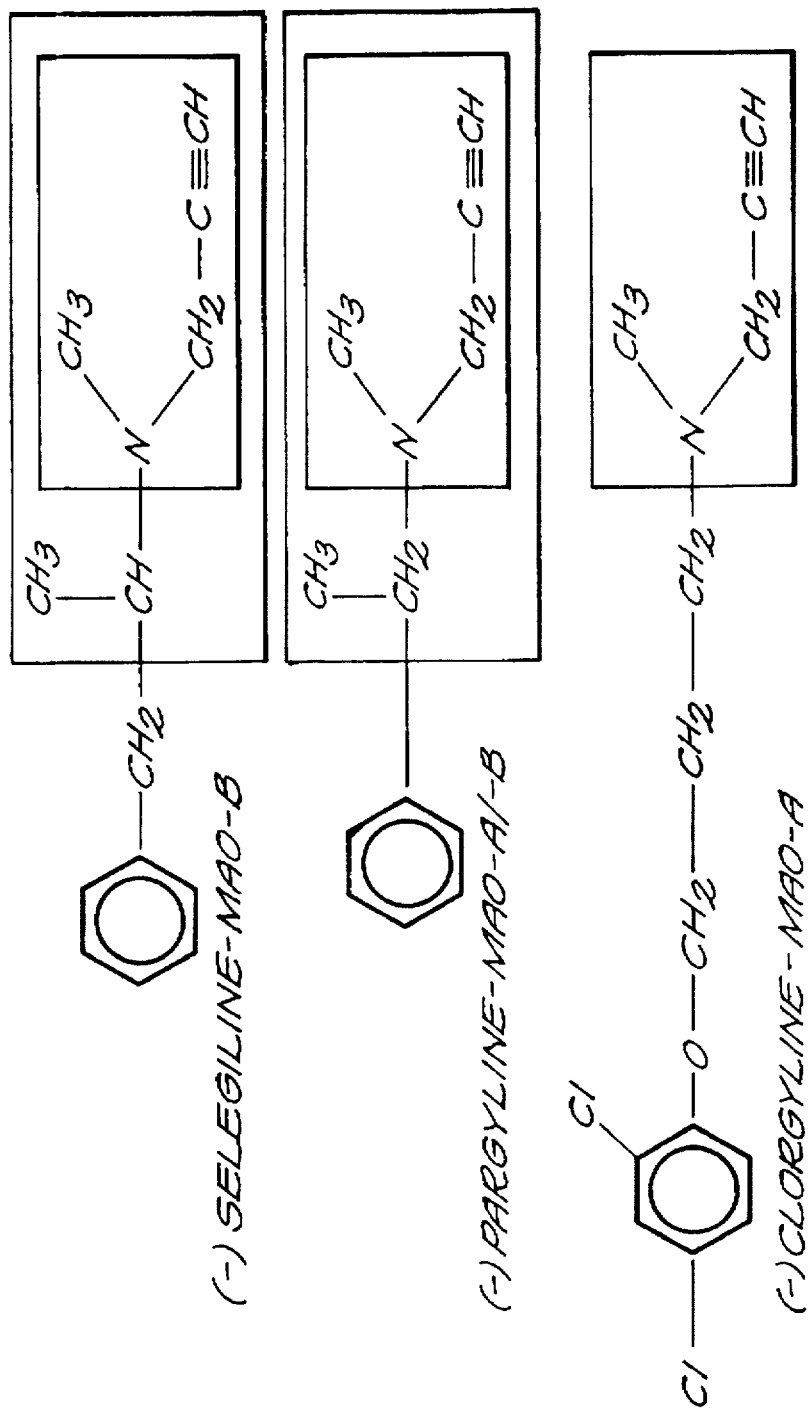
FIG. 1 shows a comparison of the known molecular structures of L-deprenyl, clorgyline and pargyline.

The present inventors have studied the time course of neuronal death induced by the neurotoxin 1-methyl-4-phenyl-1,2,5,6-tetrahydropyridine (MPTP). MPTP is oxidized, under the action of monoamine oxidase-B (MAO-B), via a dihydropyridium intermediate (MPDP+) to its toxic metabolite 1-methyl-4-phenyl-pyridinium ion (MPP+). It is believed that MPTP is converted to MPP+ in nondopaminergic cells, released and then taken up into dopaminergic neurons where it exerts its neurotoxic effects (see Vincent S. R. Neuroscience, 1989, 28 p. 189–199, Pintari, J. E. et al. Brain Res, 1983, 276(1) p. 127–140, Westlund, K. N. et al. Neuroscience, 1988, 25(2) p. 439–456, Javitch, J. A. et al. P.N.A.S. USA 1985, 82(7) P. 2173–2177, Mayor, 1986

1763, and Sonsalla, P. K. et al. 17th Annual Meeting Of The Society For Neuroscience, New Orleans, La., USA, November, 1987, 13(2)).

MPTP is rapidly metabolized and cleared in the mouse (Johannessen, J. N. et al. Life Sci. 1985, 36: p. 219–224, Markey, S. P. et al. Nature, 1984, 311 p. 465–467, Lau, Y. S. et al. Life Sci. 1988, 43(18): p. 1459–1464). In contrast to the rapid metabolism and excretion of MPTP, the present inventors have demonstrated that loss of dopaminergic neurons progresses over a period of twenty days following cessation of MPTP administration. MPTP (30 mg/kg/d) was administered i.p. to mice for five consecutive days (total cumulative dose 150 mg/kg) to produce a loss of approximately 50% of TH-immunopositive (TH+) neurons in the substantia nigra compacta (SNc) and ventral tegmental area (VTA)(see Seniuk, N. A., W. G. Tatton, and C. E. Greenwood, Brain Res., 1990, 527: p. 7–20 which are incorporated herein by reference for the relationship between MPTP dose and loss of catecholaminergic neurons). The present inventors have also found that the death of TH+ Snc neurons followed a similar timecourse. 20–30% of TH+ somata were lost by the five days after the completion of the administration of MPTP; loss of TH+ neurons continued over the next ten to fifteen days with no detectable loss thereafter. This continual loss of TH+ neurons could not be accounted for by the presence of MPP+, based on the excretion data referred to above. Joint plots of counts of TH+ and Nissl stained SNc somata also confirmed that the loss of TH+ somata represented the death of SNc neurons rather than a loss of TH immunoreactivity.

In tandem with the loss of TH+ SNc somata the present inventors have also found changes in immunodensity of TH protein in SNc and the ventral tegmental area (VTA). Cytoplasmic TH immunodensity was 40% lower in the somata of the remaining TH+ DNS neurons for MPTP-treated animals at day 5 in comparison to saline treated controls. Average somal TH-immunodensity increased over time and had reached control levels by 20 days following MPTP. Alterations in striatal DA concentrations and dopamine-dependent behaviours such as locomotion were found to parallel the changes in TH-immunochemistry. Further, the present inventors found that an increase in striatal DA content and DA synthesis as estimated by DOPAC/DA ratios also appeared to parallel behavioural recovery and indicated increased DA content and synthesis in the VTA and SNc neurons surviving MPTP exposure.

Thus, the present inventors have significantly found that following MPTP-induced neuronal damage, there is a critical 20 day period in which TH+ SNc neurons either undergo effective repair and recovery or else they die.

Most studies with deprenyl have been designed to demonstrate that inhibition of MAO-B activity in vivo blocks the conversion of MPTP to MPP+ and the neurotoxicity of MPTP. As a consequence, deprenyl was usually given either several hours or for several days prior to and then throughout MPTP administration to ensure that MAO-B activity was inhibited during the time of MPTP exposure (for example, see Cohen, G., et al., Eur. J. Pharmacol., 1984, 106: p. 209–210, Heikkila, R. E., et al., Eur. J. Pharmacol, 1985, 116(3): p. 313–318, Heikkila, R. E., et al., Nature, 1984, 311: p. 467–469 and Langston, J. W., et al., Science (Wash. D.C.), 1984, 225 (4669): p. 1480–1482). Comparable results have been obtained using other selective inhibitors of MAO-B such as AGN-1133, AGN-1135 and MD 240928 (Heikkila, R. E., et al., Eur. J. Pharmacol, 1985, 116(3): p. 313–318 and Fuller, R. W. and L. S. K. Hemrick, Life Sci, 1985, 37(12): p. 1089–1096) suggesting that the mechanism of action of deprenyl was mediated by its ability to block MAO-B and thereby prevent the toxin from being converted to its active form.

In contrast to the above studies, the present inventors were interested in determining whether deprenyl could exert an effect on DSN neurons which was independent of its ability to block MPTP conversion to MPP+. MPTP-treated mice (cumulative dose of 150 mg/kg) received deprenyl (0.01, 0.25, 10 mg/kg i.p.; 3 times per week) from day 3 to day 20 following MPTP administration. Deprenyl administration was withheld until day 3 to ensure that all mice were exposed to comparable levels of MPP+ and that all MPTP and its metabolytes had been eliminated from the central nervous system. Clorgiline, an MAO-B inhibitor, was also administered to the MPTP-treated mice.

The present inventors found that in saline treated mice, about 38% of dopaminergic substantia nigracompacta (DSN) neurons died progressively over the twenty days. The number of DSN neurons was found to be statistically the same in the MPTP-Saline and MPTP-Clorgiline treated mice. However, deprenyl increased the number of DSN neurons surviving MPTP-induced damage (16% loss—0.01 mg/kg, 16% loss—0.25 mg/kg, and 14% loss—10 mg/kg), with all doses being equipotent. Thus, the present inventors have demonstrated that deprenyl could rescue dying neurons and increase their probability of undergoing effective repair and re-establishing their synthesis of enzymes, such as tyrosine hydroxylase, necessary for dopamine synthesis. This is believed to be the first report of a peripherally or orally administered treatment which reverses the sequence of damage to death in neurons which would have otherwise died.

The inventor's studies ruled out the possibility that deprenyl was mediating its resuscitative effect through inhibition of MPTP conversion to its toxic metabolite MPP+. The results suggest that deprenyl has a previously unidentified mechanism of action. It is difficult to reconcile a direct effect of deprenyl in dopaminergic neurons themselves due to the absence of MAO-B in these cells (Vincent, S. R., Neuroscience 28, 189–199 (1989); Pintari, J. E., et al. Brain Res. 276, 127–140 (1983); Westlund, K. N. et al. Science, (Wash D.C.) 230, 181–183 (1988) and Westlund, K. N. et al. Neuroscience 25, 439–456 (1988)), making it unlikely that the results can be explained on the basis of MAO-B inhibition by deprenyl within the dopaminergic neurons themselves. Measurements of MAO-A and MAO-B in MPTP mice at the beginning and end of treatment with deprenyl (0.01 mg/Kg) showed that the 0.01 mg/Kg dose did not produce any significant MAO-A or MAO-B inhibition at the two time periods, suggesting that it is highly unlikely that deprenyl mediates its resuscitative effect thought inhibition of MAO-B. Further, clorgyline an MAO-A inhibitor did not increase the number of surviving DSN neurons after neuronal death induced by MPTP.

Other results have confirmed that the rescue of damaged neurons by deprenyl does not depend on the known MAO-B or MAO-B inhibition activity. It has been demonstrated that the rescue of axotomized motoneurons by deprenyl (see discussion below) is permanent as the motoneurons do not die when the deprenyl treatment is subsequently discontinued. It has also been demonstrated that the MAO-B inhibitor N-(2-aminoethyl)-4-chlorobenzamide hydrochloride is not effective in rescuing damaged motoneurons.

The survival of rat facial motoneurons after axotomy at 14 days of age was also examined and it was found that deprenyl increased by 2.2 times the number of motoneurons surviving 21 days after the axotomy (See Example 3 herein). Further, a dose of 0.01 mg/kg of deprenyl was just as effective as 10 mg/kg deprenyl in rescuing the motoneurons similar to the 0.01 mg/kg dose used with the MPTP model. Pargyline has also been shown to rescue motoneurons. Thus, it has been significantly demonstrated that deprenyl and pargyline can compensate in part for the loss of trophic support caused by axotomy suggesting a role for deprenyl and its analogues and derivatives in the treatment of motoneuron death in conditions such as amyotrophic lateral sclerosis.

Animals lesioned at 14 days, treated for the next 21 days with 10 mg/kg deprenyl (d14–35) and then left untreated until 65 days of age did not show any further motoneuronal death. It was also demonstrated, that the rescue is permanent for the axotomized motoneuron i.e. the motoneurons do not begin to die when deprenyl treatment is discontinued after 21 days and there is no further death over the next 30 days.

The resuscitative effect of deprenyl may be mediated by any of the cells in the nervous system and the mechanism likely involves the activation of a receptor on the cells (such as a receptor for a neuronotrophic factor) through a structure which may not be related to the structure which blocks MAO-B. This would imply that deprenyl could help prevent the death of all neurons in the brain that respond to glial trophic factors, rather than just influencing dopaminergic neurons alone. Hence as well as being therapeutically effective in Parkinson's disease, it would also be effective in other neurodegenerative and neuromuscular diseases and in brain damage due to hypoxia, ischemia, stroke or trauma and may even slow the progressive loss of neurons associated with brain aging (Coleman, P. D. & Flood D. G., Neurobiol. Aging 8, 521–845 (1987); McGeer, P. L. et al. in Parkinsonism and Aging (eds. D. B. Calne, D.C. - G. Comi and R. Horowski) 25–34 (Plenum, New York, 1989). It may also be useful in stimulating muscle reinnervation in traumatic and non-traumatic peripheral nerve damage.

The present studies also indicate that the propargyl terminus may be a factor required for the rescue of damaged neurons. As indicated above, the MAO-A inhibitor, clorgyline, at doses of 2 mg/Kg delivered every second day, did not increase the number of surviving dSNC neurons after MPTP-induced damage. A comparison of the known molecular structures of L-deprenyl and clorgyline (See FIG. 1), reveals that the compounds have the same structure in the terminal portion which contains the propargyl group (See box in FIG. 1). In contrast, the phenol ring includes the two bulky chlorines and an oxygen-linked 3 carbon chain attaches the chlorine-substituted phenol to the nitrogen with 2 carbons with a methyl side chain in L-deprenyl. The inability of clorgyline to rescue the DSN neurons may relate to the chlorines preventing the propargyl group from reaching an attachment site or may indicate that the critical structure includes the portion of the molecule linking the phenol ring to the nitrogen.

The MAO-B inhibitor N-(2-aminoethyl)-4-chlorobenzamide hydrochloride was found not to rescue immature axotomized motoneurons. The compound does not have the triple bond C ending of the propargyl terminus of deprenyl and pargyline so it appears that it attaches to a different part of the flavine portion of MAO-B.

The (+) isomer of deprenyl at a dosage of 0.01 mg/Kg was found not to rescue immature axotomized motoneurons. Thus, the optical rotation of the terminal propargyl group relative to the phenol ring and intermediate portions of the compounds may also be important for the rescue.

As discussed above, the present invention relates to the use of deprenyl or derivatives or analogues of deprenyl to rescue damaged nerve cells, to pharmaceutical compositions containing deprenyl adapted for such use; and, to methods for the treatment of disorders of the nervous system by rescuing damaged nerve cells.

Deprenyl, also known as selegiline, preferably L-deprenyl (see The Merck Index, 11th ed. 2893), derivatives of deprenyl, preferably pharmaceutically acceptable salts and esters of deprenyl; or, analogues of deprenyl, preferably structural analogues of deprenyl or functional analogues of deprenyl such as pargyline, AGN-1133, AGN-1135 and MD 240928, or other agents which may or may not inhibit MAO-B such as imipramine, chlorpromazine, amitriptyline, (−)2,3-dichloro-α-methylbenzylamine, N-cyclopropyl-substituted arylalkylamines, may be used in the present invention. Most preferably, L-deprenyl and pargyline are used in the pharmaceutical compositions, therapeutic uses and methods of the present invention.

The administration of deprenyl or derivatives or analogues of deprenyl may rescue damaged nerve cells in an animal, and thus may be used for the treatment of neurodegenerative and neuromuscular diseases and in acute damage to nervous tissue due to hypoxia, hypoglycemia, ischemic stroke or trauma. It may also be used to slow the progressive loss of neurons associated with brain aging; although the present inventors have shown that deprenyl does not prevent age-related death of mouse DSN neurons. More specifically, deprenyl may be used to treat Parkinson's disease, ALS, head trauma or spinal cord damage, patients immediately following an ischemic stroke, hypoxia due to ventilatory deficiency, drowning, prolonged convulsion, cardiac arrest, carbon monoxide exposure, exposure to toxins, or viral infections. Deprenyl or derivatives or analogues of deprenyl may also be used to stimulate muscle reinnervation in traumatic and non-traumatic peripheral nerve damage.

The pharmaceutical compositions of the invention contain deprenyl or derivatives or analogues of deprenyl, either alone or together with other active substances. Such pharmaceutical compositions can be for oral, topical, rectal, parenteral, local, inhalant or intracerebral use. They are therefore in solid or semisolid form, for example pills, tablets, creams, gelatin capsules, capsules, suppositories, soft gelatin capsules, gels, membranes, tubelets. For parenteral and intracerebral uses, those forms for intramuscular or subcutaneous administration can be used, or forms for infusion or intravenous or intracerebral injection can be used, and can therefore be prepared as solutions of the active compounds or as powders of the active compounds to be mixed with one or more pharmaceutically acceptable excipients or diluents, suitable for the aforesaid uses and with an osmolarity which is compatible with the physiological fluids. For local use, those preparations in the form of creams or ointments for topical use or in the form of sprays should be considered; for inhalant uses, preparations in the form of sprays, for example nose sprays, should be considered.

The preparations of the invention can be intended for administration to humans or animals. They contain preferably between about 1 and 4 mg of active component in the case of solutions, sprays, ointments and creams and between about 0.1% and 5% and preferably between about 0.1% and 10% of active compound in the case of solid form preparations. Dosages to be administered depend on individual needs, on the desired effect and on the chosen route of administration, but daily dosages to humans by subcutaneous, intramuscular or intracerebral injection generally vary between 0.1 and 10 mg of active substance per day, preferably between 1 to 10 mg per day, most preferably between 5 and 10 mg per day.

The pharmaceutical compositions can be prepared by per se known methods for the preparation of pharmaceutically acceptable compositions which can be administered to patients, and such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985).

On this basis, the pharmaceutical compositions include, albeit not exclusively, solutions of the deprenyl or derivatives or analogues of deprenyl in association with one or more pharmaceutically acceptable vehicles or diluents, and contained in buffered solutions with a suitable pH and iso-osmotic with the physiological fluids.

As hereinbefore mentioned the invention also relates to methods for testing a drug for activity in rescuing damaged nerve cells in a patient.

In accordance with one embodiment of the invention a method for testing a drug for activity in rescuing damaged nerve cells in a patient is provided comprising administering an agent having neurotoxic activity to a test animal; administering the drug to the test animal; sacrificing the test animal within a period of 20 days from completion of administration of the agent; taking serial sections of the brain through the substantia nigra compacta; determining the number of tyrosine hydroxlyase positive somata in alternate serial sections of the brain through the substantia nigra compacta and determining the number of Nissl stained positive substantia nigra compacta in intervening serial sections; and comparing the number of tyrosine hydroxlyase positive somata and Nissl stained somata determined with the number of tyrosine hydroxlyase positive somata and Nissl stained somata in serial sections of the brain through the substantia nigra compacta of a control animal which has not been administered the drug.

In a preferred embodiment the agent having neurotoxic activity is MPTP, most preferably in an amount of 30 mg/kg/d, which is administered i.p. to 8 week old mice, preferably C57BL mice, for five consecutive days (days −5 to 0; total preferred cumulative dose of 150 mg/kg). Three days following cessation of MPTP administration (day 0), treatment with saline (control animal) or the appropriate doses of the drug (test animals) is commenced. Preferably the administration of the drug is withheld until day 3 to ensure that all mice are exposed to comparable levels of MPP+ and that all MPTP and its metabolites have been eliminated from the central nervous system. Mice are killed by anaesthetic overdose (pentobarbital) followed by paraformaldehyde perfusion 20 days following their last MPTP injection. Brains are bisected longitudinally along the midline and the half brains are glued together using Tissue-Tek so that surface landmarks are in longitudinal register. The glued brains are frozen in −70° C. methylbutane and 10 μm serial sections are cut through the entire longitudinal length of each SNc.

The number of tyrosine hydroxlyase positive somata in serial sections of the brain through the substantia nigra compacta may preferably be determined using a polyclonal TH antibody as the primary antibody and a standard avidin-biotin reaction with diaminobenzidine (DAB) as the chromogen for visualization as generally described in Seniuk, N. A. et al. Brain Res. 527, 7–20 (1990) and Tatton, W. G. et al. Brain Res. 527, 21–32 (1990) which are incorporated herein by reference, and modified as follows. Slide-mounted sections are incubated with unlabelled primary TH antisera in 0.2% Triton/0.1M phosphate buffer at 4° C. overnight. Tissues are washed with phosphate buffer then incubated for 1 hour with biotinylated goat anti-rabbit IgG secondary antibody followed by avidin-HRP incubation. A 0.05% solution of DAB in 0.01% hydrogen peroxide is used to visualize the immunoreactive somata.

Intervening sections may be Nissl stained to define nuclear outlines following the procedure set forth in Seniuk et al., Brain Res. 527: 7, 1990 and Tatton et al. Brain Res. 527:21, 1990 which are incorporated herein by reference.

In accordance with another embodiment of the invention a method for testing a drug for activity in rescuing damaged nerve cells in a patient is provided comprising carrying out an axotomy on a test animal; administering the drug to the test animal; determining the number of choline acetyl transferase positive somata for histological sections from the site of the axotomy; and comparing the number of choline acetyl transferase positive somata determined with a number of choline acetyl transferase positive somata in serial sections from the site of the axotomy in a control animal which has not been administered the drug.

Preferably a unilateral facial nerve transection is carried out on the test animal, preferably a rat, and paired lesion and no lesion groups are treated with saline (control animal) or appropriate doses of the drug (test animal). The rats are sacrificed at 21 days after axotomy and serial coronal histological sections of the brainstem at the level of the facial nuclei are processed for choline acetyl transferase (ChAT) immunocytochemistry using the procedure of Tatton W. G. et al, Brain Res. 527:21, 1990, which is incorporated herein by reference.

The following non-limiting examples are illustrative of the present invention:

EXAMPLES

Example 1

This example demonstrates the loss of tyrosine hydroxylase immunopositive (TH+) neurons from the substantia nigra compacta (SNc) following the administration of MPTP and their rescue by deprenyl.

In the first part of the study, the time course of MPTP induced neuronal death was established as follows. MPTP (30 mg/kg/d) was administered i.p. to 8 week old isogenic C57BL mice (from the National Institutes of Aging colony at Jackson Laboratories, USA (C57BL/NNia)); (n=6/time period) for five consecutive days (total cumulative dose of 150 mg/kg). Mice were killed by anaesthetic overdose (pentobarbital) followed by perfusion with isotonic saline (containing 5% rheomacrodex and 0.008% xylocane) and 4% paraformaldehyde 5, 10, 15, 20, 37 and 60 days following their last MPTP injection. Dissected brains were immersed in 4% paraformaldehyde in 0.1 m phosphate buffer overnight and placed in 20% sucrose.

In the second part of the study, the rescue by deprenyl of TH+ SNc neurons from MPTP induced loss was demonstrated as follows. MPTP (30 mg/kg/d) was administered i.p. to 8 week old C57BL mice (n=6–8/treatment group) for five consecutive days (days −5 to 0; total cumulative dose of 150 mg/kg). Three days following cessation of MPTP administration (day 0), mice were treated with saline, deprenyl (Deprenyl Canada) (0.01, 0.25 or 10 mg/kg i.p.) or Clorgiline (Sigma Chemical Company, U.S.A.) (2 mg/kg) three times per week. Deprenyl administration was withheld until day 3 to ensure that all mice were exposed to comparable levels of MPP+ and that all MPTP and its metabolites had been eliminated from the central nervous system. Doses of deprenyl were chosen to reflect those used in studies demonstrating that deprenyl can prolong the lifespan of the rat and inhibit MAO-B activity by approximately 75% but have no effect on MAO-B activity (0.25 mg/kg) or cause inhibition of both MAO-B and MAO-A (10 mg/kg) (Knoll, J. Mt. Sinai J. Med. 55, 67–74 (1988) and Knoll, J. Mech. Ageing Dev. 46, 237–262 (1988), Demarest, K. T. and Azzarg A. J. In: Monoamine Oxidase: Structure, Function and Altered Function (T. P. Singer, R. W. Von Korff, D. L. Murphy (Eds)), Academic Press, New York (1979) p. 423–430). A dose of 0.01 mg/kg deprenyl was also chosen; at this dose less than $10^{-7}$M will reach the brain tissue. As a further control, mice were treated with only deprenyl and were not administered MPTP. Mice were killed by anaesthetic overdose (pentobarbital) followed by paraformaldehyde perfusion 20 days following their last MPTP injection.

For both parts of the study, brains were bisected longitudinally along the midline and the half brains were glued together using Tissue-Tek so that surface landmarks were in longitudinal register. The glued brains were frozen in $-70°$ C. methylbutane and then 10 µm serial sections were cut through the entire longitudinal length of each SNc.

Alternate sections were processed for TH immunocytochemistry using a polyclonal TH antibody as the primary antibody and a standard avidin-biotin reaction (ABC kit, Vector Labs) with diaminobenzidine (DAB) as the chromogen for visualization as generally described in Seniuk, N. A. et al. Brain Res. 527, 7–20 (1990) and Tatton, W. G. et al. Brain Res. 527, 21–32 (1990) which are incorporated herein by reference, and modified as follows. Slide-mounted sections were incubated with unlabelled primary TH antisera (Eugene Tech) in 0.2% Triton/0.1M phosphate buffer at $4°$ C. overnight. Tissues were washed with phosphate buffer then incubated for 1 hour with biotinylated goat anti-rabbit IgG secondary antibody followed by avidin-HRP incubation. A 0.05% solution of DAB in 0.01% hydrogen peroxide was used to visualize the immunoreactive somata. For comparative optical density measurements, sections from control and MPTP-treated brains were mounted on the same slide to reduce the effect of slide to slide variability in the assay procedure and were processed for immunocytochemistry.

Figure 2:
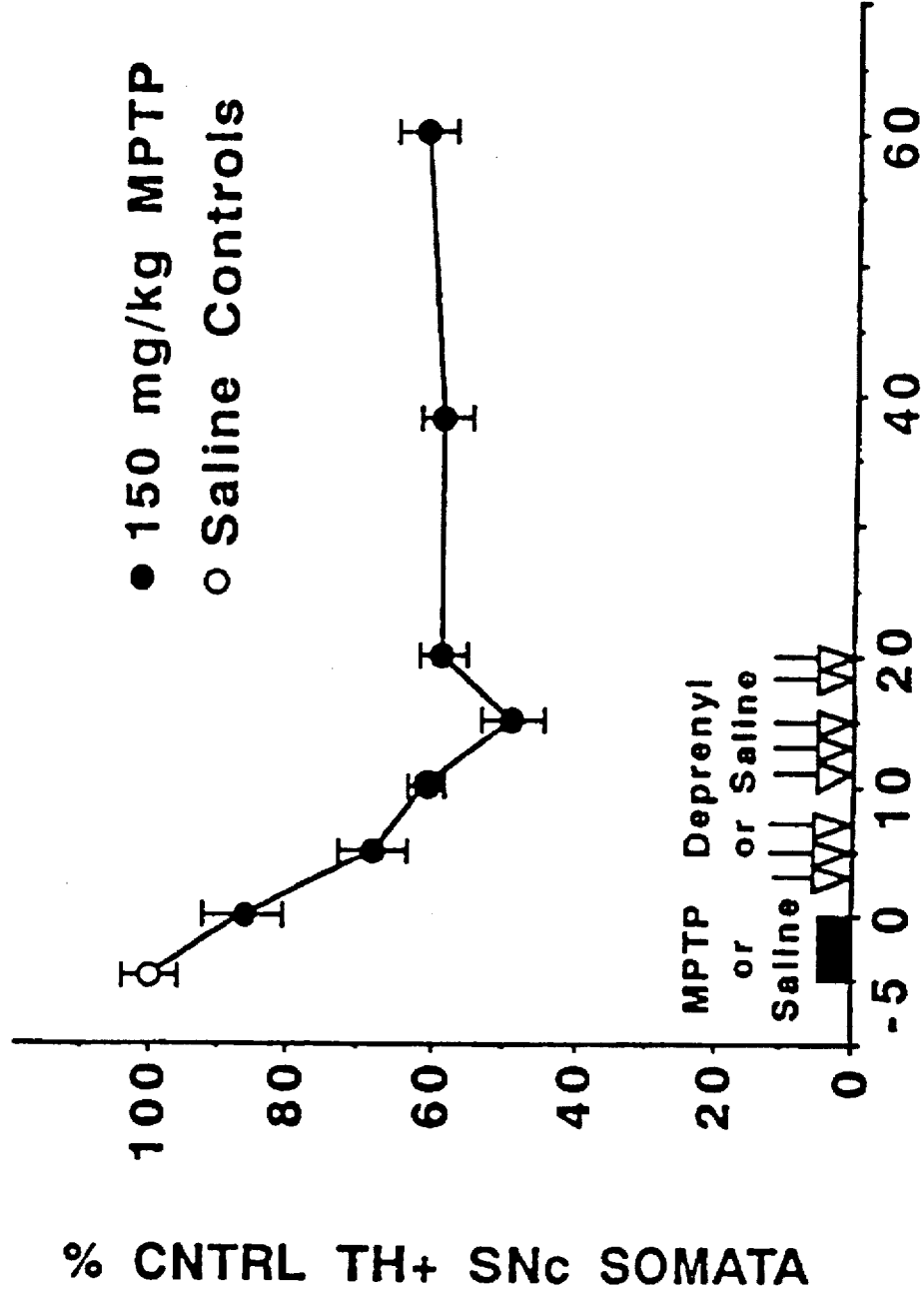
FIG. 2 is a graph showing the numbers of tyrosine hydroxylase immunopositive (TH+) neurons in the substantia nigra compacta (SNc) following the administration of MPTP.

The number of TH+ SNc neurons was obtained by counts of number coded alternate serial sections through each entire nucleus. Sections were recounted by multiple blind observers to check any observer bias. The values were corrected for section thickness (Konigsmark, B. W. In: Nauta, W. H., Ebesson S. O. E. ed Contemporary Research Methods in Neuroanatomy, New York, Springer Verlag, p. 315–380, 1970). The mean value plus or minus the standard error of the mean was computed for the saline injected control mice. Subsequent data was then expressed as a percentage of this mean number as shown in FIG. 2.

Intervening sections were Nissl stained to define nuclear outlines (See Seniuk et al., Brain Res. 527: 7, 1990; Tatton et al. Brain Res. 527:21, 1990 which are incorporated herein by reference). The paired half sections for the glued half brains insured that any differences in neuronal numbers in the experimental and control groups were not due to different penetration or exposure to the antibodies or the reagents.

On 20 randomly-chosen half sections through the length of each nucleus for each animal, the region containing TH+ somata was traced using a camera lucida attachment to the microscope and the outline was then transposed to the immediately adjacent Nissl section using local histological features for landmarks (each nucleus usually included about 90 pairs of sections). The numbers of Nissl somata containing a nucleolus within the outline were counted according to three size groups (small—140 to 280 µm², medium—300 to 540 µm² and large—540 to 840 µm²), excluding glial profiles (40 to 100 µm²), using criteria similar to those of the rat SNc (Poirier et al. 1983 Brain Res. Bull. 11:371). Numbers of TH+ somata were plotted against numbers of Nissl somata for the corresponding areas of 20 immediately adjacent sections. The joint Nissl/TH+ counts provide a means for determining whether reductions in the numbers of TH+ SNc somata are due to neuronal destruction or a loss of TH immunoreactivity by surviving neurons (see Seniuk et al. 1990, supra, for details as to rationale for the procedure).

Figures 3, 3A:
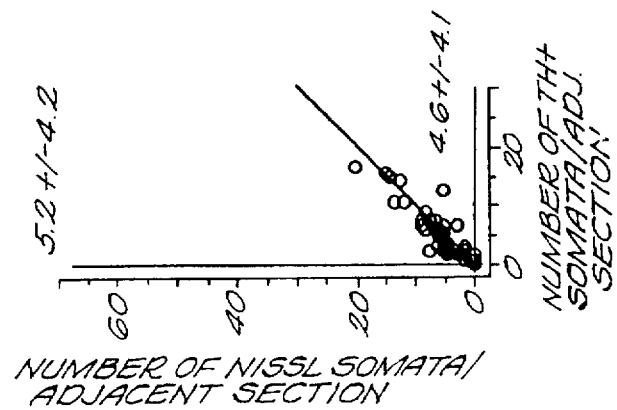
FIG. 3 are joint plots of the counts of TH+ and Nissl stained SNc somata from corresponding areas of immediately adjacent sections for Saline Only treated (A1,A2,A3), MPTP-Saline treated (B1,B2,B3) and MPTP-Deprenyl treated animals (C1,C2,C3) with the data pooled from 3 animals in each group at 20 days following the MPTP treatment.
Figures 2, 3A:
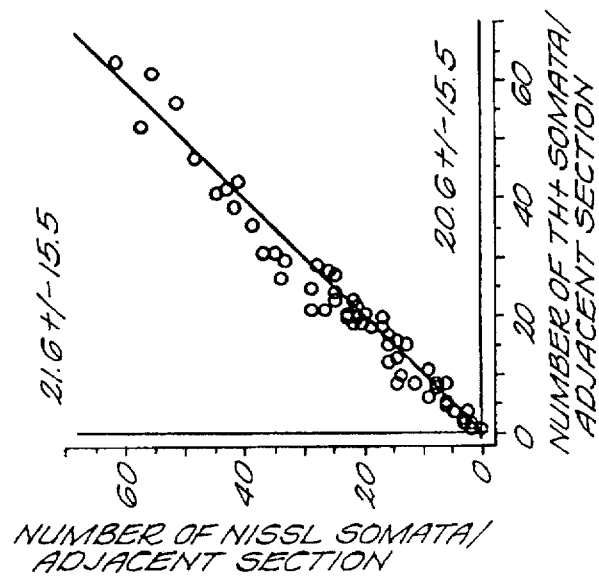
Figures 1, 3A:
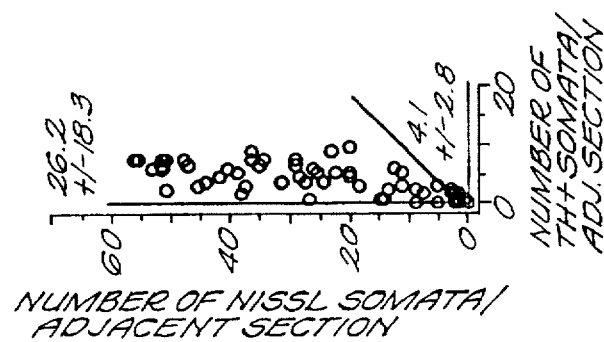

FIG. 3 shows a loss of TH+ somata from the SNc from days 0 to 20 post MPTP, with no decline thereafter. 20 to 30% of TH+ somata were lost by five days after completion of the injection schedule (day 5); loss of TH+ neurons continued over the next ten to fifteen days with no further disappearance thereafter. This continual loss of TH+ neurons could not be accounted for by the presence of MPTP or its toxic metabolite MPP+, due to its rapid elimination from the body (Johannessen, J. N. et al., Life Sci. 36, 219–224 (1985); Markey, S. P. et al., Nature, 311, 465–467 (1984); and Lau et al., Life Sci. 43, 1459–1464 (1988)). Some neurons have the capacity to initiate repair following axonal damage, such as that seen with MPTP, by reactivating DNA transcription "programs" similar to those utilized by developing neurons to extend their axons or neurites (see Barron, K. V. in Nerve, Organ and Tissue Regeneration: Research Perspectives (eds. Seil, F. J.), 3–38 (Academic Press, New York, 1986). In the case of the TH+ SNc neurons, it would appear that a critical 20 day period exists in which these neurons either undergo effective repair and recovery following MPTP-induced damage or they die.

Joint plots of the counts of TH+ and Nissl stained SNc somata from corresponding areas of immediately adjacent sections in mice treated with saline only (values for three animals are pooled in FIGS. 3A1–A3) show that the numbers of TH+ somata are linearly related to the number of Nissl somata and are closely scattered around an equal value diagonal (illustrated by the diagonal lines in FIG. 3) for the medium-sized SNc somata (FIG. 3A2)) and the large-sized SNc somata (FIG. 3A3). In each plot in FIG. 3, the mean ±1.0 standard deviation for the Nissl counts and the TH+ counts of somata per half section are shown at the upper end of each Y axis and the right end of each X axis respectively. For the medium and large somata the mean number of Nissl somata exceed the corresponding mean number of TH+ somata by 5–10% which appears to correspond to the percentage of nigrostriatal neurons which are not TH+ (Van der Kooy et al. Neuroscience 28:189, 1981).

Figures 3, 3B:
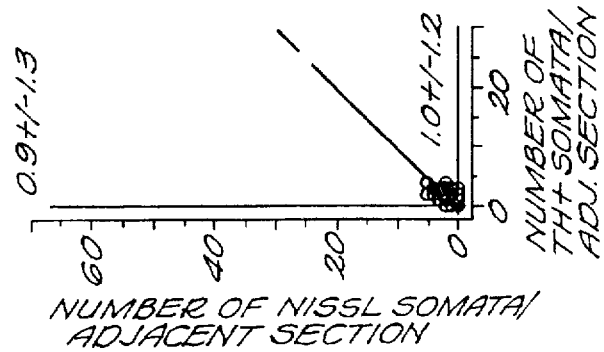
Figures 2, 3B:
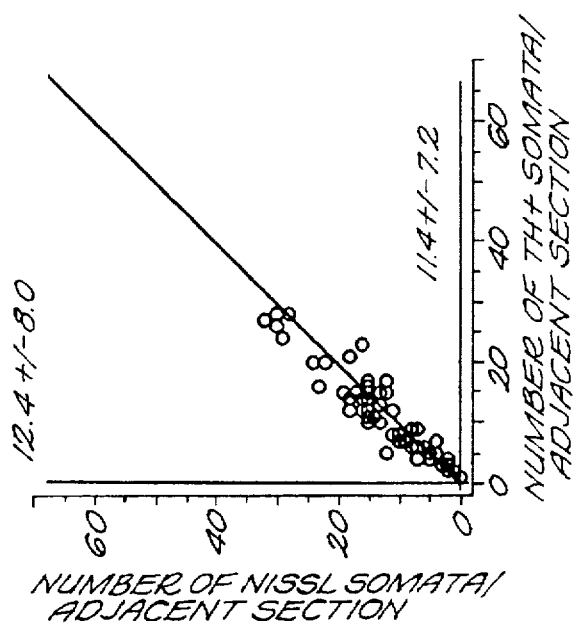
Figures 1, 3B:
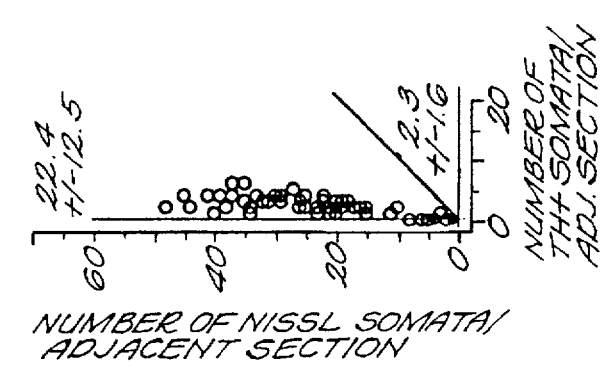

Joint counts of the small-sized SNc somata in the saline treated animals show that only a small proportion of the small neurons are TH immunoreactive and therefore dopaminergic (FIG. 3A1). These results are in keeping with previous findings in rodents which indicate that the large and medium sized somata are those of dopaminergic nigrostriatal neurons while the smaller somata are largely those of locally ramifying interneurons (Van der Kooy et al., 1981 supra; Poirier et al. Brain Res. Bull. 11:371, 1983). Joint Nissl/TH counts of somata in the animals treated with MPTP alone or MPTP followed by saline (values for three MPTP-saline animals are pooled in FIGS. 3B1, 3B2 and 3B3) confirmed that by 20 days after the completion of the MPTP treatment the loss of TH+ somata represented the death of SNc neurons rather than a loss of TH immunoreactivity in surviving neurons. FIG. 3B2 and 3B3 show that even though the counts of Nissl and TH+ somata are reduced from 21.6±15.5 and 20.6±15.5 per section to 12.4±8.0 and 11.4±7.2 for the medium-sized and large-sized somata respectfully (values are means ±1.0 standard deviation), the almost equal value relationships between the counts were maintained. If the SNc neurons were losing TH immunoreactivity but not dying, the scatter of the joint plots would be expected to shift to loci above the equal value diagonal (Seniuk et al. Brain Res. 527:7, 1990). Furthermore, FIG. 3B1 shows that the numbers of small-sized Nissl stained somata decreased slightly (26.2±18.3 to 22.4±12.5 per section) in accord with the reduction (4.1±2.8 to 2.3±1.6 per section) in the TH+ component of the small-sized SNc somata. If some of the losses of medium and large sized SNc somata were due to atrophy so that their cross-sectional areas no longer fell within the medium and large size ranges in response to the MPTP treatment, one would expect an increase in the numbers of small sized Nissl stained somata.

Figure 4C:
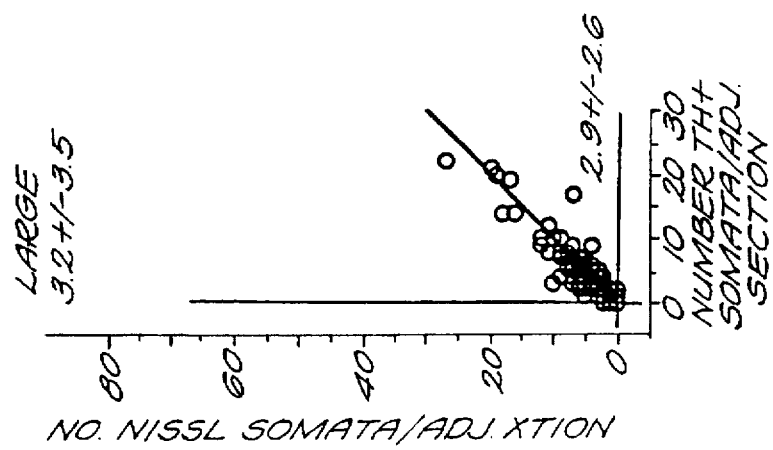
FIG. 4 are joint Nissl/TH+ plots for days 0, 3, 5, 10, 15 and 20 for pooled saline controls.
Figure 4B:
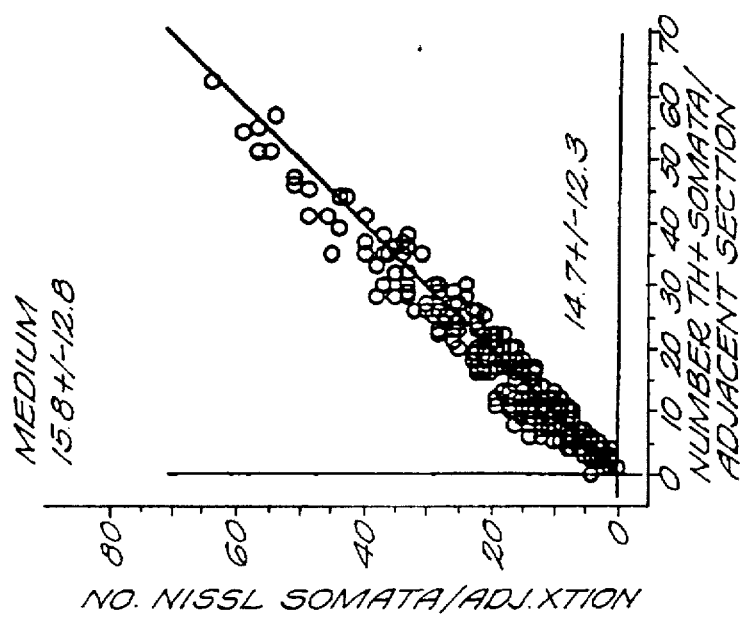
Figure 4A:
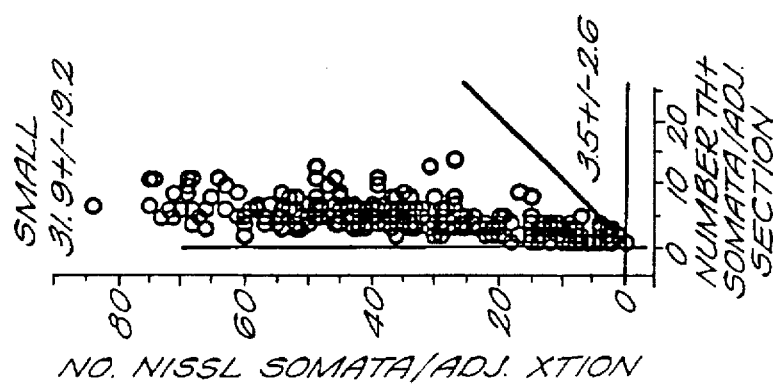
Figure 5A:
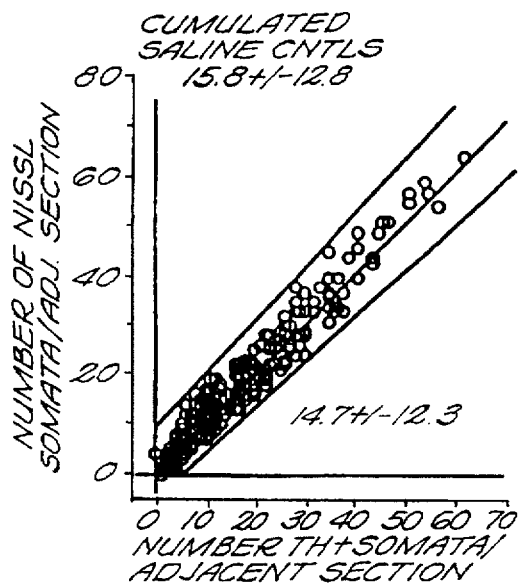
FIG. 5 are joint Nissl/TH+ plots for cumulated saline controls and for days 0,5,10,15, and 20 after completion of MPTP treatment.
Figure 5B:
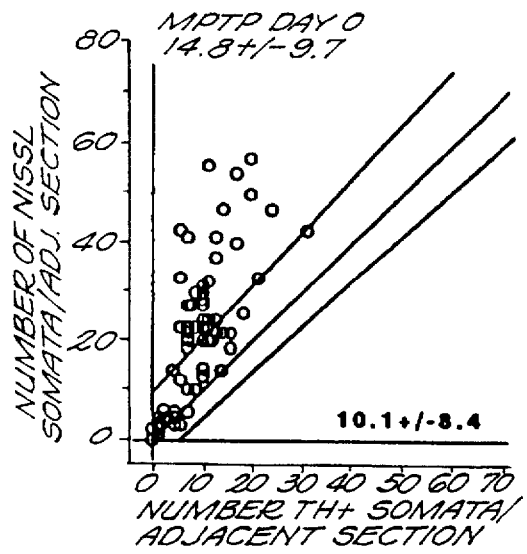
Figure 5C:
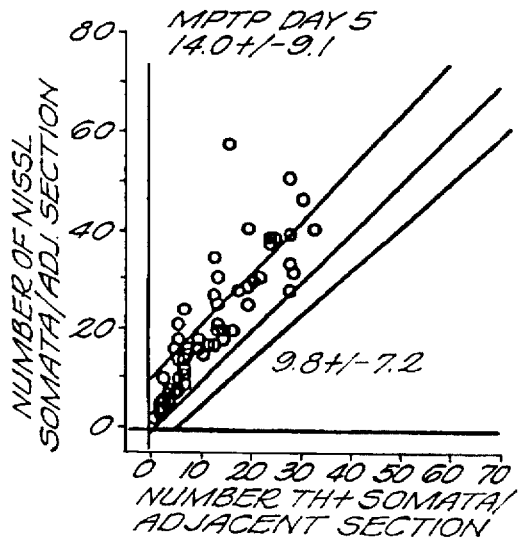
Figure 5D:
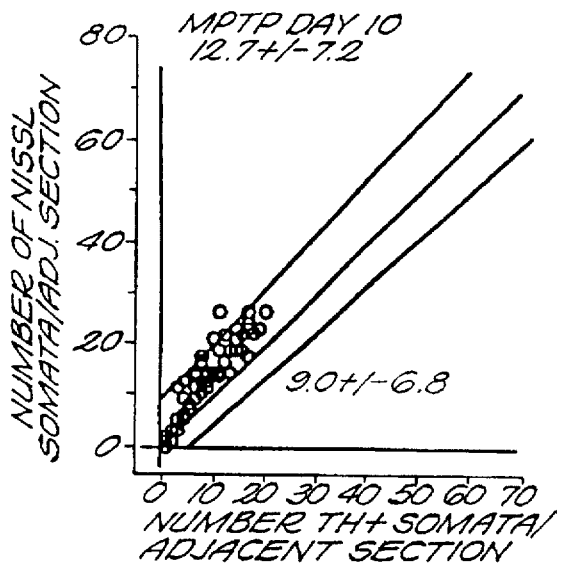
Figure 5E:
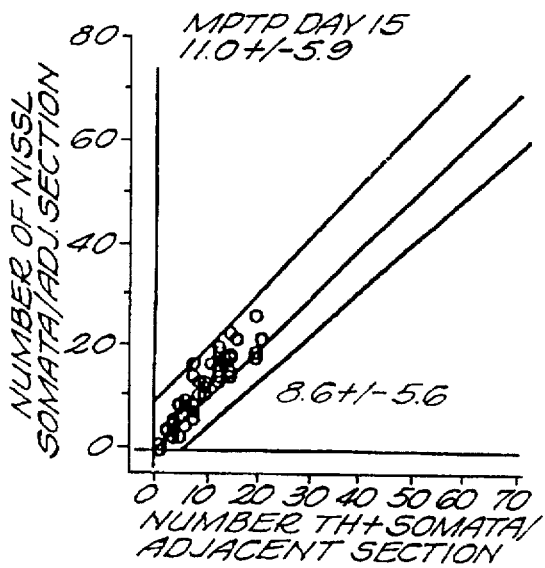
Figure 5F:
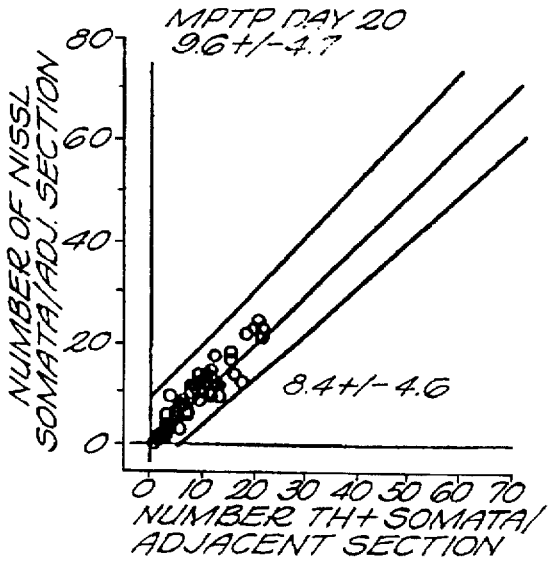

Joint Nissl/TH+ plots for days 0, 3, 5, 10, 15 and 20 after completion of the MPTP treatment and for the saline controls are shown in FIGS. 4 and 5.

FIG. 4 represents Nissl/TH plots for the three major size groups of SNc somata in rodents (small cross sectional somal areas, 140–280 $\mu m^2$, medium cross sectional somal areas, 300–540 $\mu m^2$ and large cross sectional somal areas, 540–840 $\mu m^2$) for the saline control animals. The data was pooled for saline controls sacrificed at days 0, 3, 5, 10, 15 and 20 after completion of the MPTP exposure. As previously shown, the joint Nissl/TH+ plots for the small SNc somata largely fall above the equal value diagonal (mean values of 31.9±19.2 per section for Nissl counts and 3.5±2.6 for TH+ counts) since most of the small somata are those of non-dopaminergic neurons. In contrast, the medium and large somata which are known to be largely dopaminergic cluster closely about the equal value diagonal (Nissl mean/section of 15.8±12.8 and TH+ mean/section of 14.7±12.3 for the medium-sized somata and Nissl mean/section of 3.2±3.5 and TH+ mean/section of 2.9±2.4 for the large-sized somata). Hence for the saline controls the great majority of medium sized and large-sized Nissl stainable somata are also TH immunoreactive.

FIG. 5 shows that at Day 0 (the final day of the MPTP exposure), a major proportion of plots for the medium-sized somata (medium-sized somata account for more than 90% of the dSNc neurons) fall above the equal value diagonal and above the range of the points established for the saline treated animals. This indicates that a significant proportion of the medium-sized dSNc neurons have lost detectable TH immunoreactivity but have not yet died at Day 0 (compare the mean Nissl counts/section for the pooled saline controls of 15.8±12.8 to that for the Day 0 MPTP exposed of 14.8±9.7 showing that 14.8/15.8 of the medium sized somata are still present at Day 0). Gradually for days 5 through 20 the locus of the points return to within the band established for the saline controls while the extent of the points along the equal value diagonal shrinks toward the origin of the plots. That progressive change in the loci of the points in the joint Nissl/TH+ plots indicates that the neurons are gradually dying over the 20 day period so that by day 20 all of the surviving medium-sized neurons have detectable TH immunoreactivity.

Figure 6:
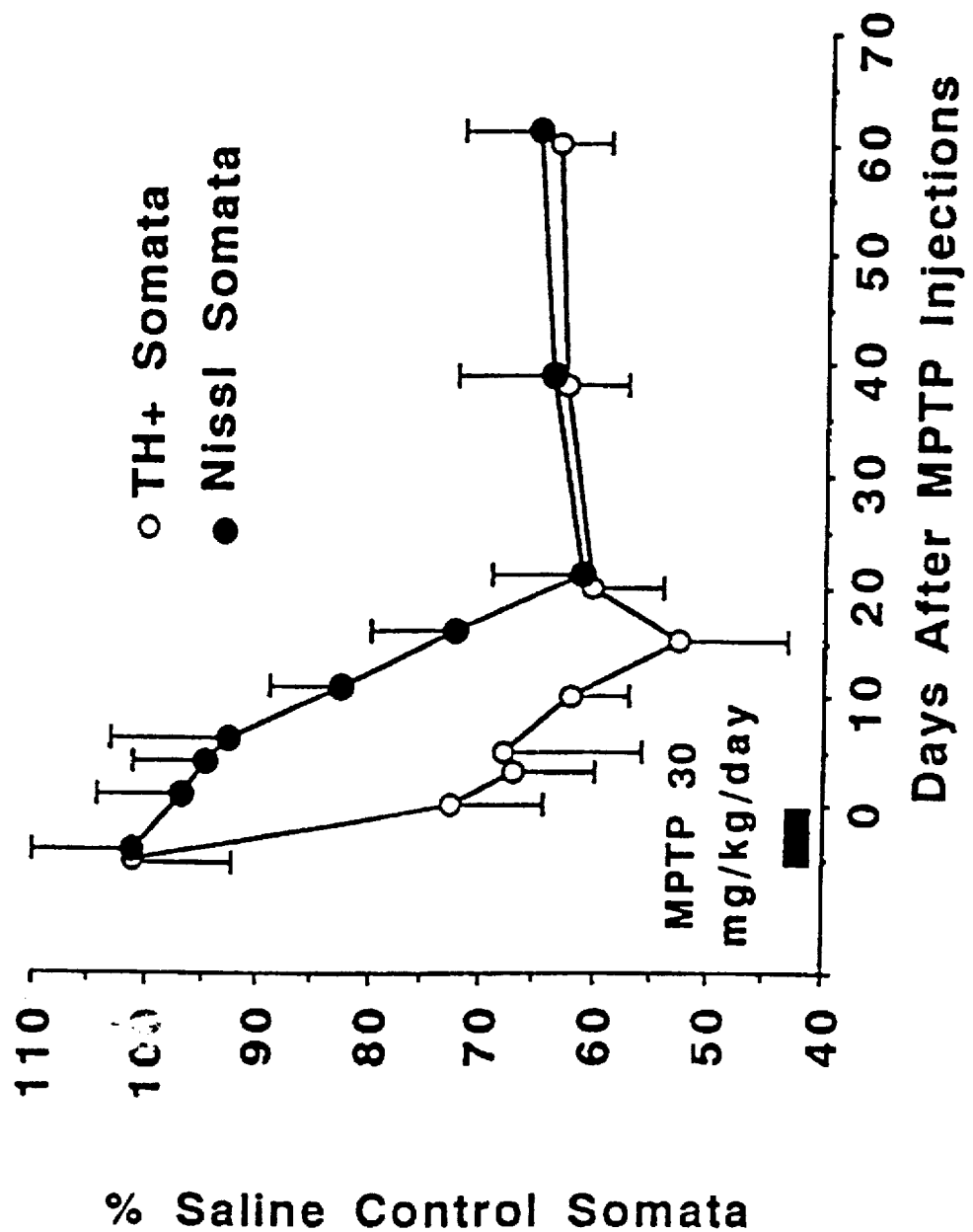
FIG. 6 shows superimposed plots for the percentage of Nissl stained somata and the percentage of TH+ immunoreactive somata relative to the mean values for the saline controls for Day 0 through Day 60.

FIG. 6 shows superimposed plots for the percentage of Nissl stained somata and the percentage of TH immunoreactive somata relative to the mean values for the saline controls for Day 0 through Day 60. The difference between the TH immunoreactive percentages and the Nissl-stained percentages demonstrates the percentage of dSNc neurons which are sufficiently damaged to suspend TH synthesis but have not died due to the toxin. Hence at Day 3, when the deprenyl treatment was initiated, an average of 37% of the dSNc somata had lost detectable TH immunoreactivity but only 4% had died. The two plots converge between days 15 and 20 when the percentage of TH immunoreactive somata is not different from the number of Nissl stainable SNc somata. The difference between the two plots can be taken to estimate the percentage of severely damaged dSNc neurons that are potentially rescuable at each time point after MPTP exposure.

According to the superimposed plots in FIG. 6, 84% of the dSNc neurons that died by days 15–20 could potentially be rescued at Day 3. Hence, since it was found that deprenyl rescued 66% of that 84%, deprenyl treatment in fact rescued 79% of the neurons that had not died before therapy was initiated.

Figure 7:
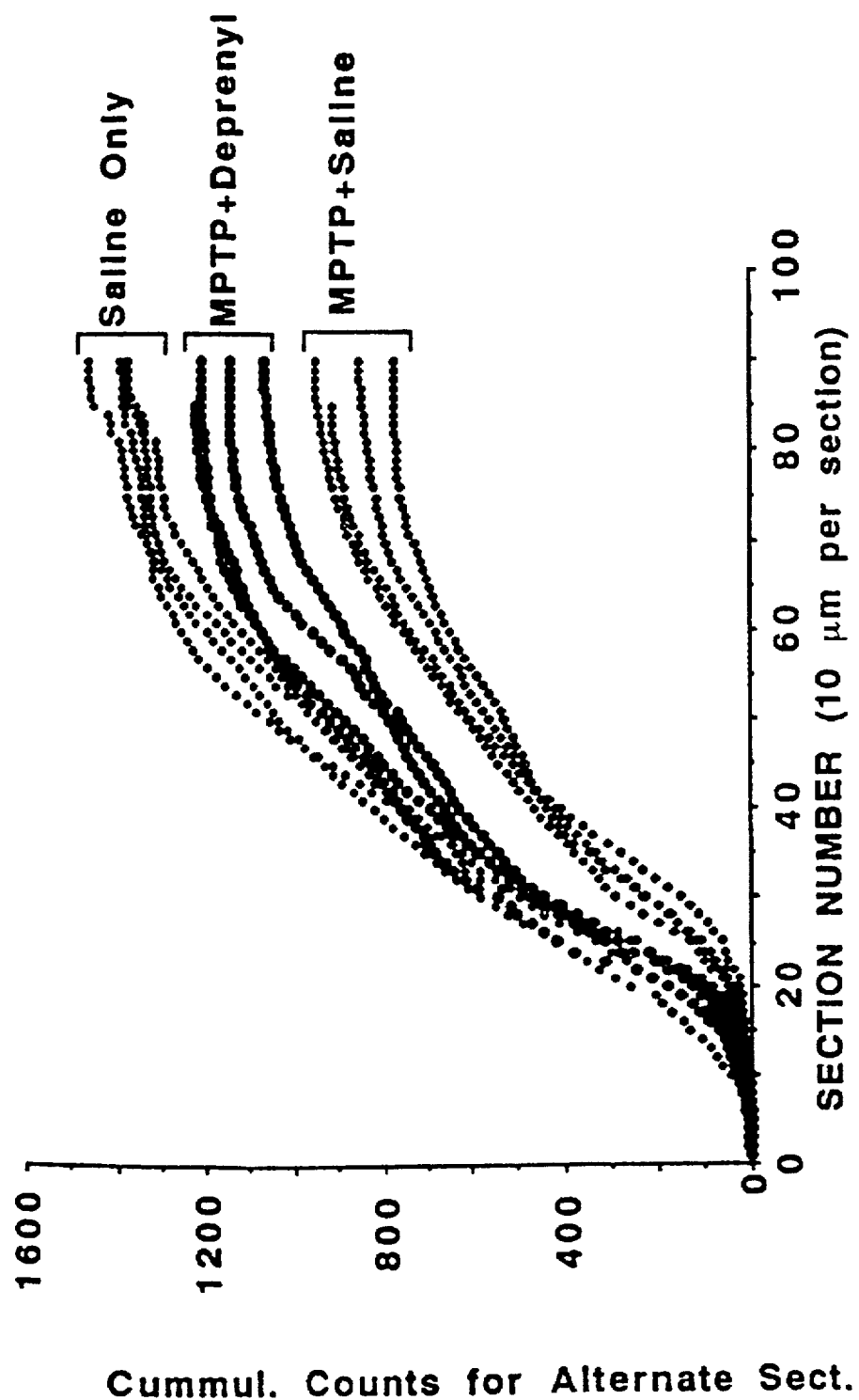
FIG. 7 is a graph showing the cumulative counts of TH+ SNC neurons versus section number for individual representative SNc nuclei taken from alternate 10 micron serial sections throughout the entire nucleus.
Figure 8:
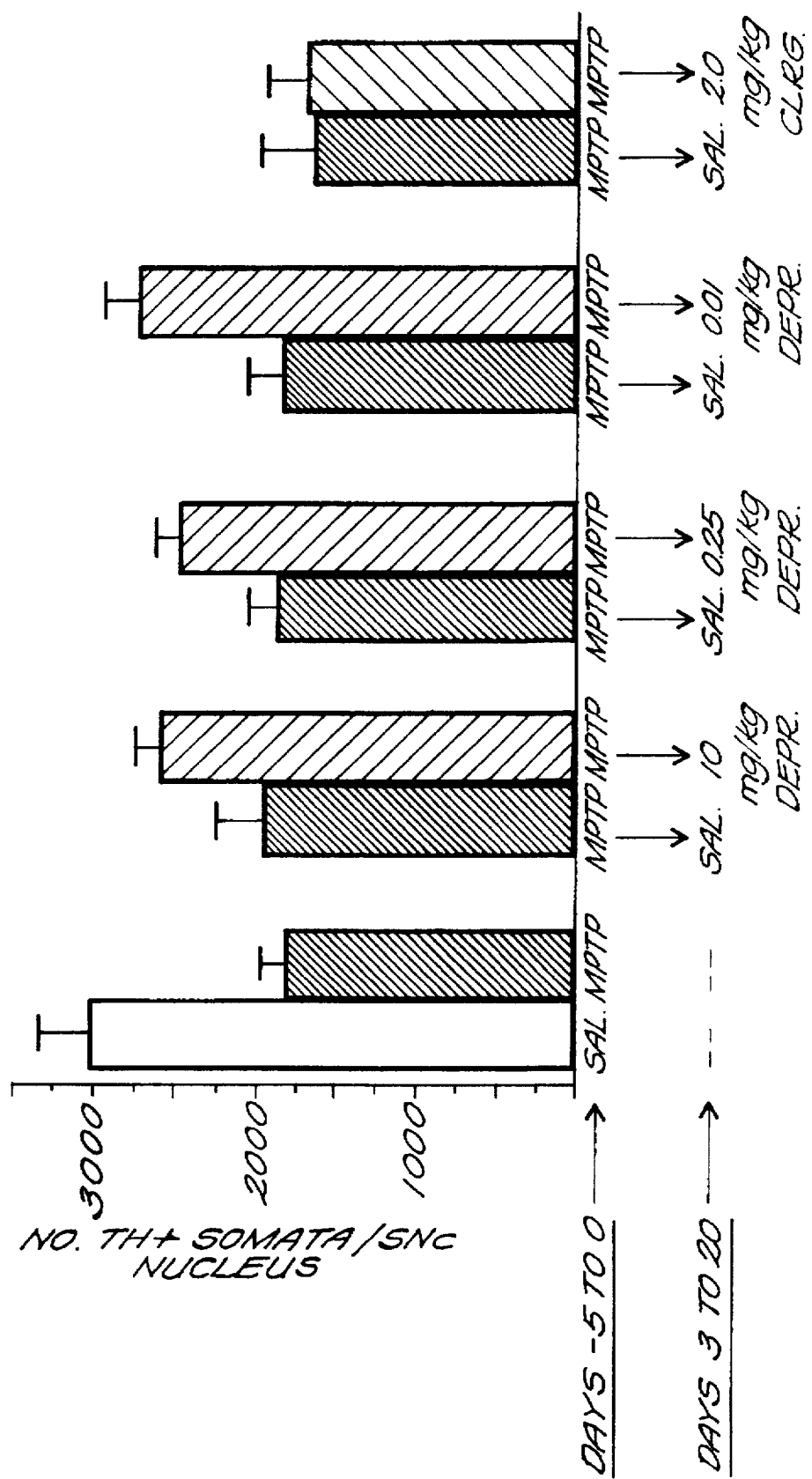
FIG. 8 is a graph showing the mean and SEM values for the MPTP, MPTP-Saline and MPTP-deprenyl treated mice.

FIG. 7 presents the raw counts of TH+ SNc somata for individual SNc nuclei taken from alternate 10 micron serial sections throughout the entire rostro-caudal length of each nucleus and expressed as a cumulative frequency distribution. Four representative trials for each treatment are presented in FIG. 7. Values for neuronal counts from mice treated with saline alone, MPTP (150 mg/kg) and saline and MPTP plus deprenyl (0.25 mg/kg, 3 times per week) are shared with those presented in histogram fashion in FIG. 8. As shown in FIG. 8, the cumulative frequency distribution curves for all SNc nuclei (n=4/treatment group) have a similar pattern indicating that the loss of TH+ somata following MPTP and their rescue by deprenyl occurred in all parts of the nuclei although it appears to be greatest in the rostral portion of the nuclei (sections 10–40) that contains neurons which are relatively more resistant to the toxin. FIG. 8 also illustrates that there is no overlap in individual frequency distribution curves between the three groups of animals.

Figure 9A:
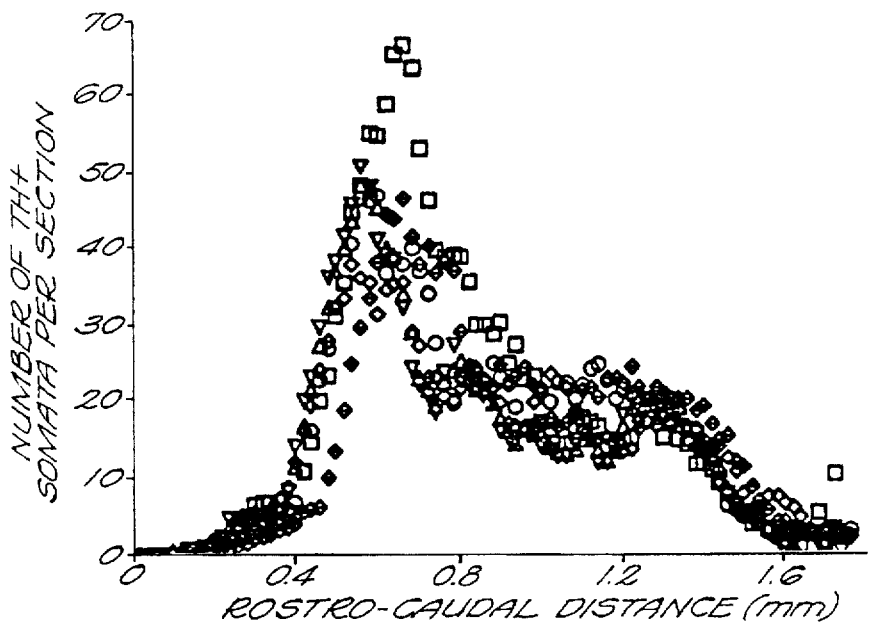
FIG. 9 is a graph showing TH+ somal counts for SNC neurons along the rostrocaudal length of a nucleus.
Figure 9B:
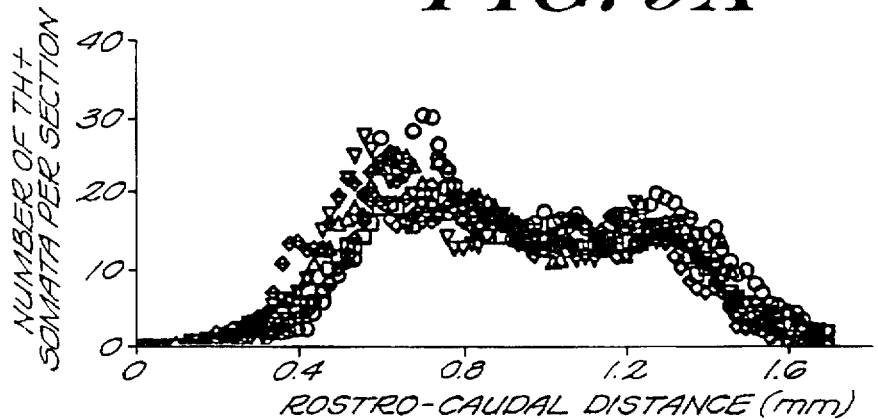
Figure 9C:
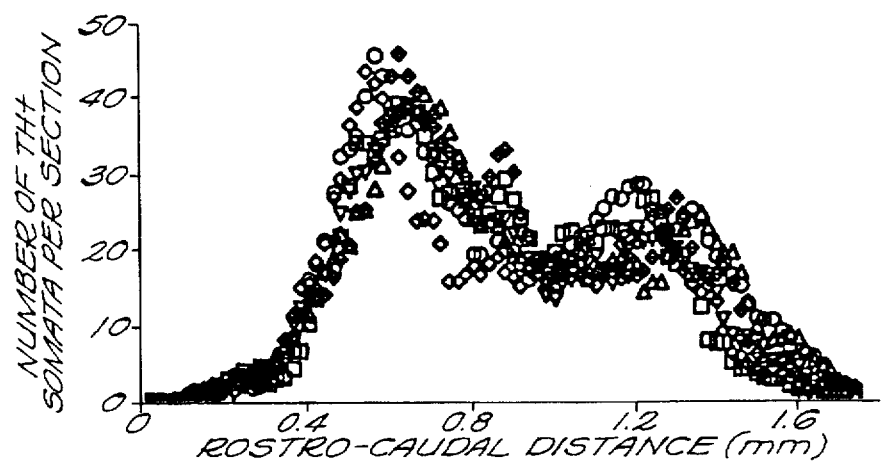

FIG. 9 shows TH+ somal counts for dSNC neurons along the rostrocaudal length of a nucleus. Rostrocaudal counts for 6 animals are superimposed in each panel. The area under each represents the total number of immunoreactive dSNC neurons and it shows the rescue by deprenyl.

Data shown in FIG. 8 represent the average number for all trials (n=6–8 mice/treatment group, i.e. 12–16 SNc nuclei) ±S.E.M. of TH+ somata/SNc nucleus. To obtain these values, raw counts of TH+ somata were converted to neuronal numbers using a correction factor of 2.15 as described by Konigsmark, B. W., in Contemporary Research Methods in Neuroanatomy (eds. Nauta, W. H. and Ebesson SOE) 315–380 (Springer Verlag, New York, 1970). FIG. 8 shows an increased number of TH+ SNc somata in the deprenyl treated mice relative to animals receiving MPTP alone, suggesting that deprenyl prevented a portion of the neuronal loss associated with MPTP-induced toxicity. Both low and high doses of deprenyl were equipotent in preventing the TH+ SNc neuronal loss.

In particular FIG. 8 shows that the mean corrected numbers of TH+ somata found for animals treated with saline only of 3014±304 (mean±SEM) were significantly reduced (Mann-Whitney Test, p<0.001) in the animals treated with MPTP only (1756±161) and the MPTP-Saline groups (1872±187, 1904±308 and 1805±185). Therefore MPTP caused average losses of 36, 38 and 42% of TH+ somata in those three MPTP pretreated groups (black bars in FIG. 8).

All the MPTP saline control groups are statistically the same (p>0.05). FIG. 8 also shows that Clorgiline an MAO-A inhibitor does not rescue the neurons since the MPTP-Saline (1706±155) and MPTP-Clorgyline (1725±213.6) values are statistically the same.

Deprenyl significantly increased (p<0.005) the number of TH+ SNc somata after MPTP to 2586±161 (14% loss), 2535±169 (16% loss) and 2747±145 for the 10, 0.25 and 0.01 mg/kg doses respectively. Hence all doses of deprenyl reduced the loss of TH+ somata caused by the MPTP to less than 50% of the loss that was found when the MPTP was followed by saline i.e. all three deprenyl doses produce similar and statistically significant (p<0.001) increases in neuronal numbers compared to the saline treated animals.

Figure 10:
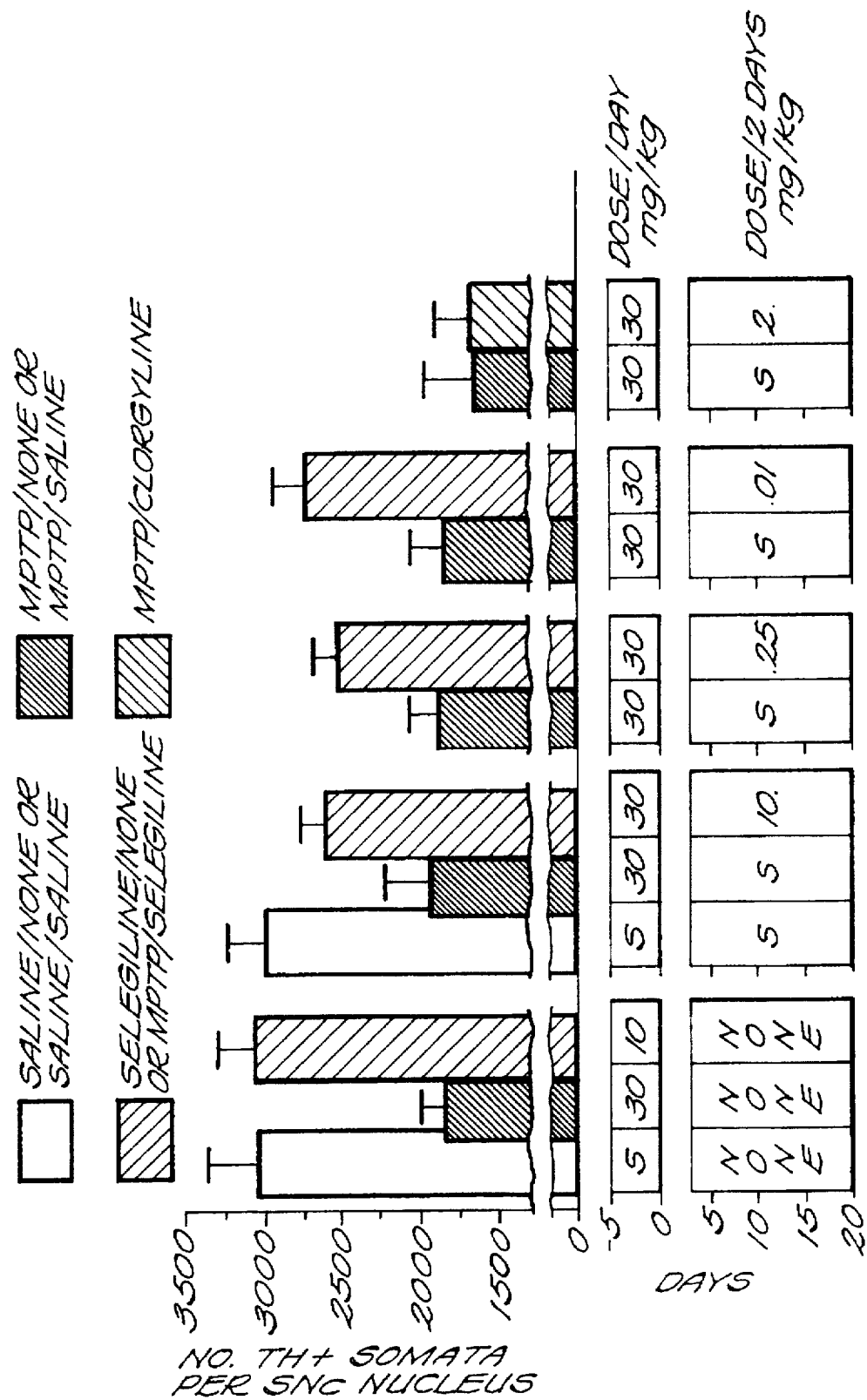
FIG. 10 is a graph showing the mean corrected number of TH+ somata for saline, MPTP, MPTP-saline, MPTP-clorgyline and MPTP-deprenyl treated animals with a table illustrating the timing of the various treatments.

FIG. 10 also shows the mean corrected number of TH+ somata found for animals treated with saline only, MPTP only, MPTP-saline, MPTP-clorgyline, MPTP-deprenyl with a table illustrating the timing of the various treatments. It also shows somal counts for animals only treated with deprenyl. Deprenyl alone does not alter the counts of TH+ somata in animals not previously exposed to MPTP.

The results illustrated in FIGS. 7 and 8 are even more striking when one considers the time-course of MPTP-induced loss of TH+ SNc neurons discussed above. By day five 75% of the TH+ SNc neurons which would die by day twenty had already lost their TH-immunoreactivity and only 25% of the TH+ SNc neurons which would die continued to loose TH-immunoreactivity between days 5 and 20. Assuming that the time course of neuronal loss was identical in the first and second part of the study, the numbers of TH+ SNc somata would have decreased from a mean of 3014 somata/nucleus to 2169 at day 3 and then further declined to an average of 1872 somata/nucleus by day 20. Deprenyl-treated mice (0.25 mg/kg) had an average of 2535 somata/nucleus thereby showing that deprenyl rescued all TH+ SNc neurons that would have died during the 17 days of administration and may even have rescued some TH+ SNc neurons which were no longer identifiable by TH+ immunocytochemistry.

Figures 3, 3C:
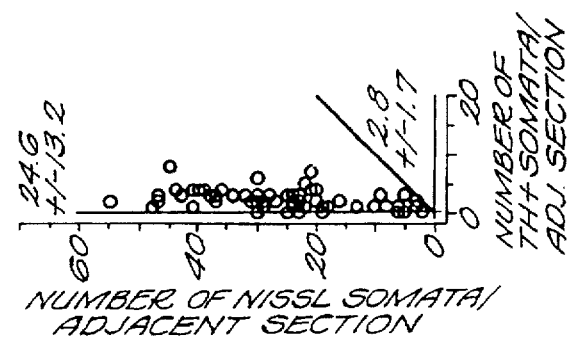
Figures 2, 3C:
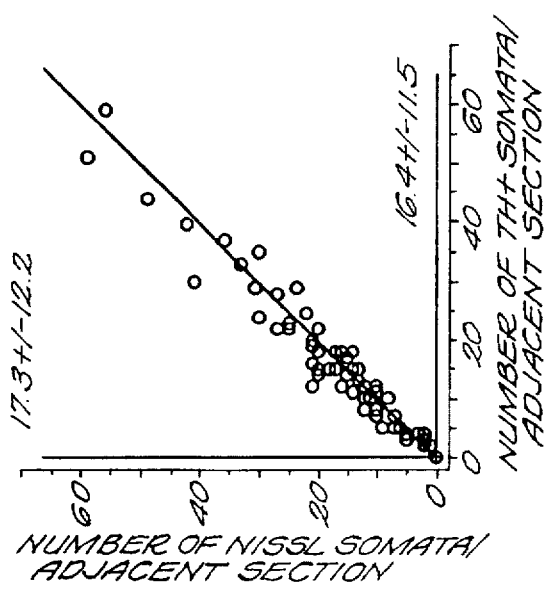
Figures 1, 3C:
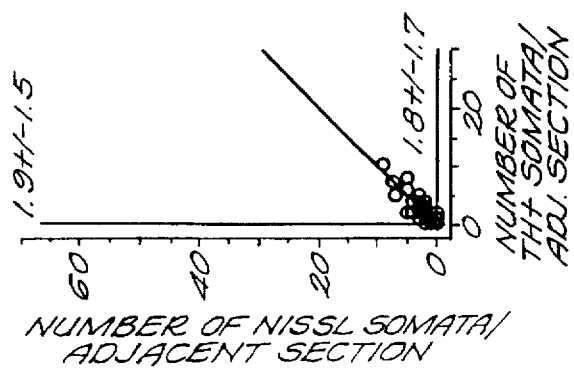

The joint Nissl/TH+ counts in FIGS. 3C1–C3 were plotted for pooled data from three animals treated with MPTP followed by 0.25 mg/kg doses of deprenyl. FIG. 3C2 shows a joint reduction in the loss of Nissl and TH+ medium-sized SNc somata compared to that for the MPTP-saline animals (FIG. 3B2). There is a relatively smaller reduction in the loss of large-sized somata for the MPTP-deprenyl animals (FIG. 3C3) compared to that for the MPTP-saline animals (FIG. 3B3). The joint Nissl/TH+ plots establish that reduced loss of TH+ SNc somata in the MPTP-deprenyl treated mice is due to reduction in neuronal death rather than a reduction in the number of neurons which are not TH immunoreactive.

Example 2

MPTP-Mice were administered deprenyl (0.01 mg/dg or 0.25 mg/kg) following the procedure set out in Example 1. MAO-A and MAO-B measurements were obtained in accordance with the method set out below 24 hours after the first 0.25 mg/kg or 0.01 mg/kg deprenyl administration and 18 days later (corresponding to day 21 which would be just after the animals were sacrificed for the immunochemistry at day 20).

MAO activity was assayed in fresh tissue homogenates by the method of Wurtman, R. J. and Axelrod, J., (Biochem Pharmacol 1963;12:1439–1444), with a modification of substrates in order to distinguish between MAO-A- and MAO-B. This method relies on the extraction of acidic metabolites of either (14-C)-serotonin (for MAO-A) or (14-C) phenylethylamine (for MAO-B) in toluene/ethyl acetate. Tissue homogenates were incubated in potassium phosphate buffer containing either radiolabelled serotonin (100 micromolar) or phenylethylamine (12.5 micromolar) for 30 minutes at 37° C. The reaction was stopped by the addition of HCl and acid metabolites extracted into toluene/ethyl acetate. Radioactivity in the toluene/ethyl acetate layer is determined by liquid scintillation spectrometry. Blanks are obtained from either boiled tissue homogenates or form reaction mixtures containing enzyme (Crane, S. B. and Greenwood, C. E. Dietary Fat Source Influences Mitochondrial Monoamine Oxidase Activity and Macronutrient Selection in Rats. Pharmacol Biochem Behav 1987;27:1–6).

Figure 11:
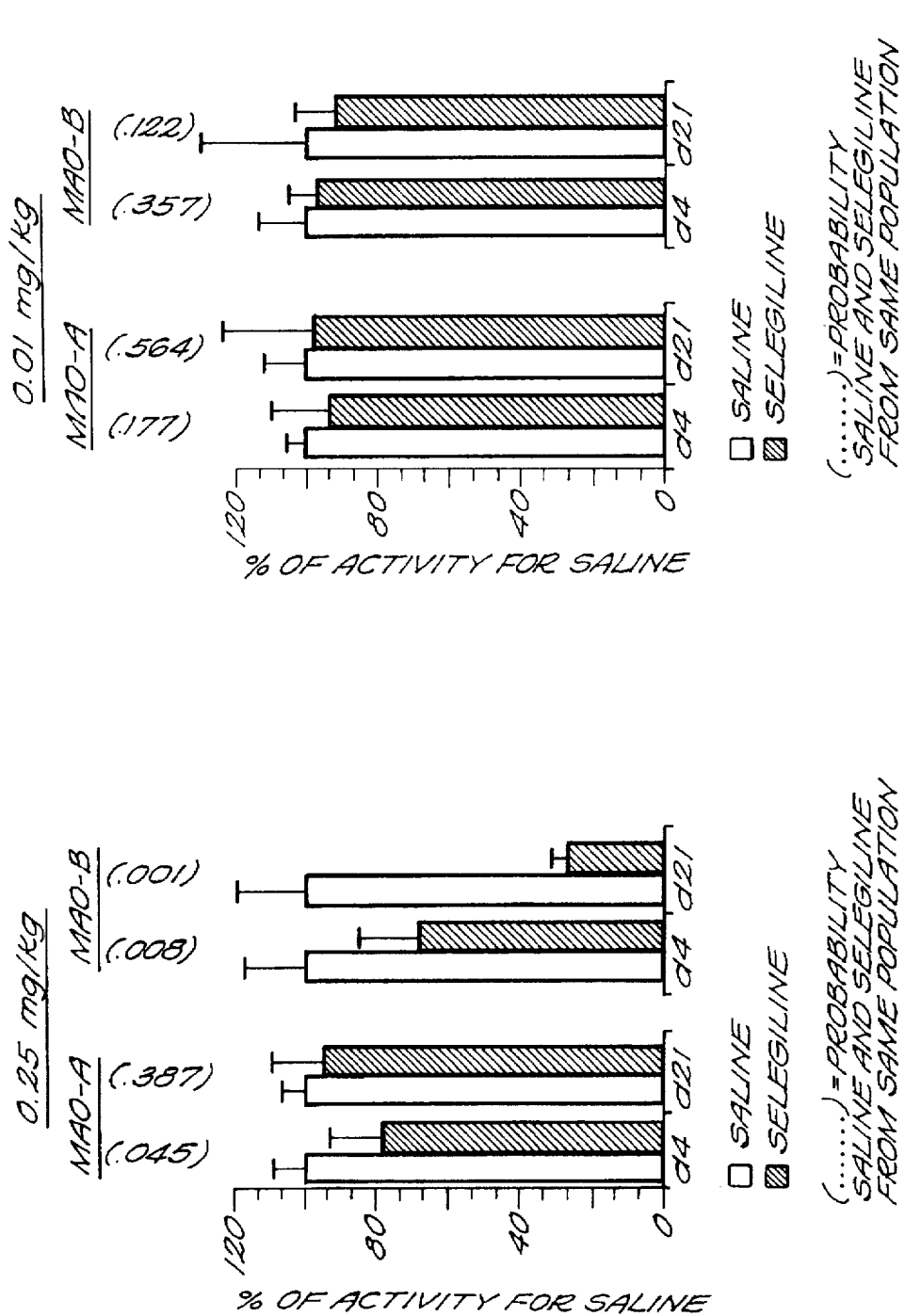
FIG. 11 is a bar graph showing MAO-A and MAO-B measurements at 24 hours (d4) after the first administration of deprenyl (0.25 mg/kg or 0.01 mg/kg) and 18 days later (d22)

FIG. 11 presents the MAO-A and MAO-B measurements for 24 hours after the first 0.25 mg/kg or 0.01 mg/kg and 18 days later (corresponding to day 21 which would be just after the animals were sacrificed for the immunocytochemistry at day 20). Hence since MAO-B inhibition (100%—MAO-B activity) would gradually increase over the 17 day treatment period, the two measures (labelled d4 and d22 to correspond to FIG. 2) give a picture of MAO-A and MAO-B activity at the beginning and end of the treatment period.

The KS probability shown in the brackets above each pair (saline and deprenyl treatment) represents the results of the Kolmogorov-Smirnov two sample nonparametric statistical testing (Siegel, S. Non Parametric Statistics for the Behavioral Sciences, McGraw-Hill Book Company, New York, 1956, pp. 127–136) to determine if the deprenyl-saline pairs are drawn from the same population. The probability value indicates the probability that the data comes from the same population. A value of p<0.5 is required to detect any significant differences and p<0.01 is preferable. Hence there is weak but detectable inhibition of MAO-A at d4 for the 0.25 mg/kg deprenyl dose which may be real since the MAO-B inhibitor may cause weak MAO-A inhibition at higher doses. The 0.25 mg/dose causes strong MAO-B inhibition at both d4 (72% activity, 28% inhibition) and d22 (31% activity, 69% inhibition). Ninety percent or more MAO-inhibition was required for anti-depressant effects but conceivably 28 to 69% MAO-B inhibition might mediate the rescue at deprenyl doses of 0.25 mg/kg.

Most importantly, the 0.01 mg/kg dose did not produce any significant MAO-A or MAO-B inhibition at d4 and d22. Hence the marked rescue with 0.01 mg/kg is equipotent to that with 0.25 mg/kg but cannot be due to MAO-B inhibition. Therefore, deprenyl may activate a receptor through a 3D structure which may not be related to the structure which blocks MAO-B.

Example 3

Male, C57BL/6J mice obtained at five weeks of age from Jackson Labs (Bar Harbour, Me.) were housed in individual cages and allowed food and water ad libitum. Mice were given an initial two week acclimatization period to a 12:12 hour light:dark (LD) cycle in an isolated room kept at a constant temperature of 21° C. Subjective 'day' began at 8:00 hours while subjective 'night' began at 20:00 hours. Light levels were maintained at 200 lux during the subjective day. Locomotory movements were selectively quantified with a Stoelting Electronic Activity Monitor, individual sensor boxes being placed under each cage. Higher frequency signal interruption such as feeding or grooming events were not recorded. Locomotory movements for individual mice were continuously monitored under continual darkness (DD) or under LD conditions for 90 to 120 days. After approximately 20 days the mice were treated with twice daily injections for 5 days (pre injection days −5 to 0) of saline or MPTP (to achieve cumulative doses of 37.5, 75, 150 and 300 mg/kg). Injections were always given during the subjective day, the first injection occurring 4 hours after 'lights on' and the second, 4 hours before 'lights off'.

Spectral analysis (Bloomfield, P. Fourier Analysis of Time Series: An Introduction; John Wylie and Sons: New York, 1976, Brigham, E. O. The Fast Fourier Transform; Prentice-Hall, New York, 1974, Marmarelis, P. Z.; Marmarelis, V. Z. Analysis of Physiological Systems—The White-Noise Approach; Plenum Press: New York and London, 1978) of the locomotory activity was done with a SYSTAT statistical software program using fast Fourier transforms. Activity counts from periods just exceeding 240 hours (about 10 days) or 120 hours (about 5 days) were used. The number of samples were chosen to just exceed 128 or 256 in order to fulfil the rule of powers of 2. Before Fourier decomposition the activity values were treated with a split-cosine-bell taper to reduce leakage from strong components into other components. These values were then padded with zeros to 512 samples. The mean was then removed from these values and the Fourier transform was calculated for 100 lags to encompass hours/cycle values of 5.12 to 512. The magnitudes were squared to determine the power of each component and the power for each hour/cycle value was expressed as a percentage of the total power.

Neurochemical assays were performed at 5, 10, 15 and 20 days following the last of the MPTP injections. The mice were sacrificed by cervical dislocation and the brain removed. Striatal tissue was dissected so as to include the nucleus accumbens and the caudate. The tissue was frozen in 2-methylbutane (Kodak) at −70° C. until their catecholamine concentrations were measured by reverse-phase ion-pair high performance liquid chromatography (HPLC) with electrochemical detection. Tissue samples were weighed, then homogenized in 0.2N perchloric acid containing dihydroxybenzylamine as internal standard and extracted onto alumina (Mefford, I. N. J. Neurosci. Meth. 1981, 3, 207–224). The catecholamines were desorbed into 0.1N phosphoric acid, filtered and injected onto an Ultrasphere ODS 5 um column. The mobile phase contained 7.1 g/l Na2HPO4, 50 mg/l EDTA, 100 mg/l sodium octyl sulphate and 10% methanol. The detector potential was +0.72 versus a Ag-AgCl reference electrode. Interrun variability was approximately 5%.

Figure 12:
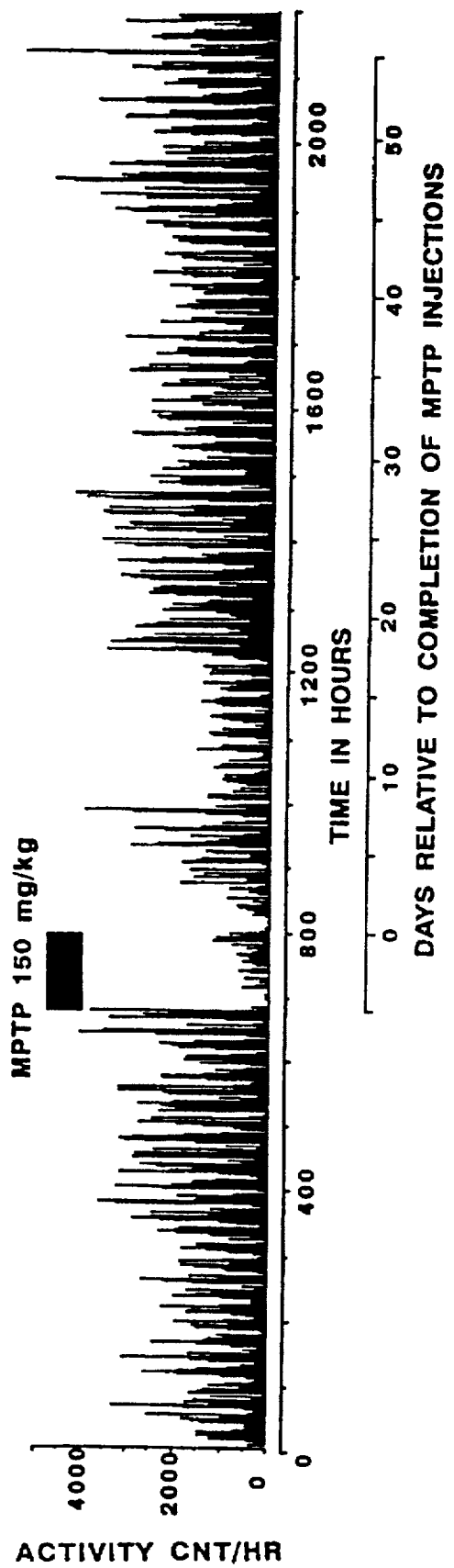
FIG. 12 shows a spectral analysis of locomotory activity for mice injected with MPTP.

FIG. 12 shows 92 days of typical recording and the black bar indicates the interval of MPTP injection (150 mg/kg in total, 30 mg/kg daily for five days). Each vertical bar on the activity trace represents the sum of activity for one hour. Note that there is a slower rhythm with a period between 100–200 hours superimposed on a faster (about 24 hour) circadian rhythm which introduces a cyclic variation into the amplitude of the activity peaks. The regularity of these patterns, as well as the amplitude of activity, was significantly affected during the MPTP injection period (675 h–842 h), but seemed to "recover" by 1200 hours, viz. between days 15–20 post-injection.

Figure 13A:
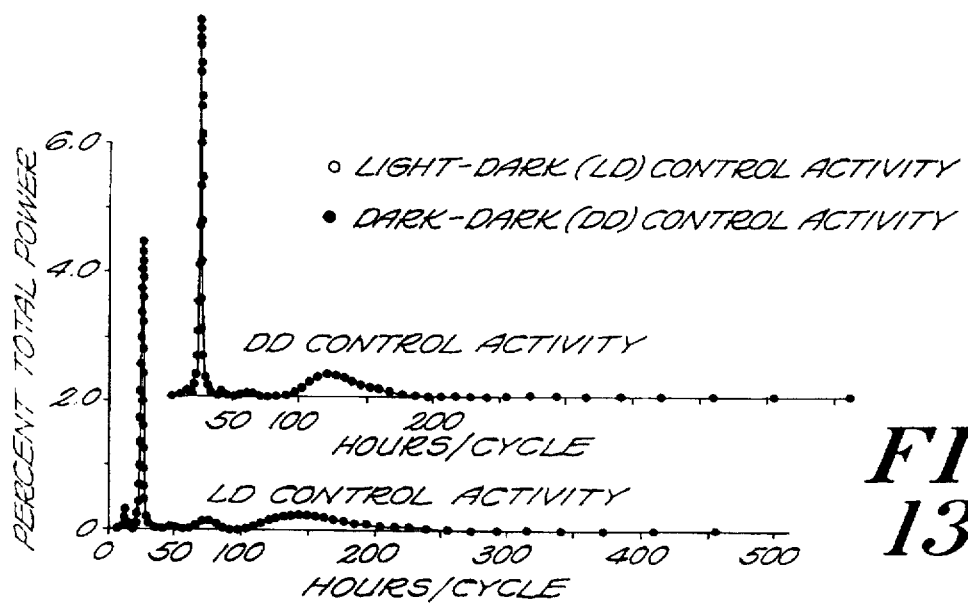
FIG. 13 shows high resolution power spectra for LD and DD preinjection control period from a saline injected mouse.
Figure 13B:
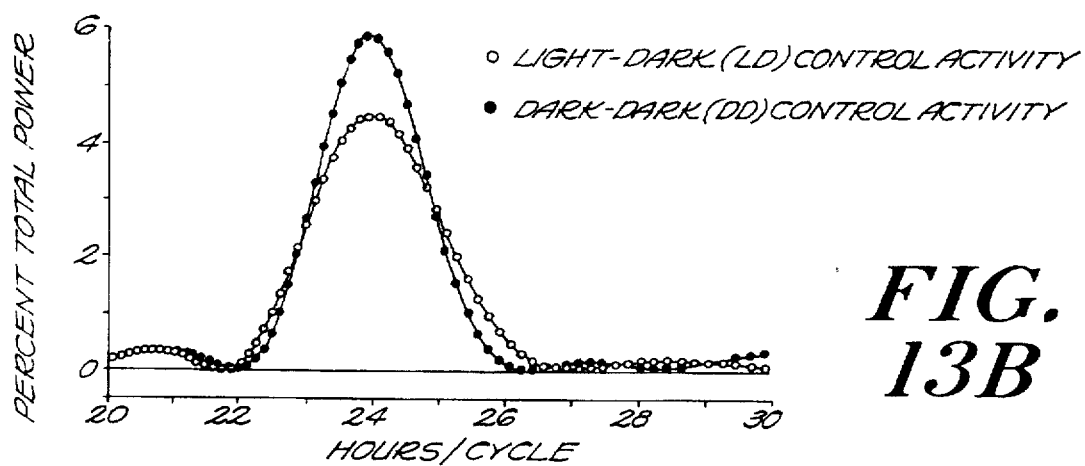
Figure 13C:
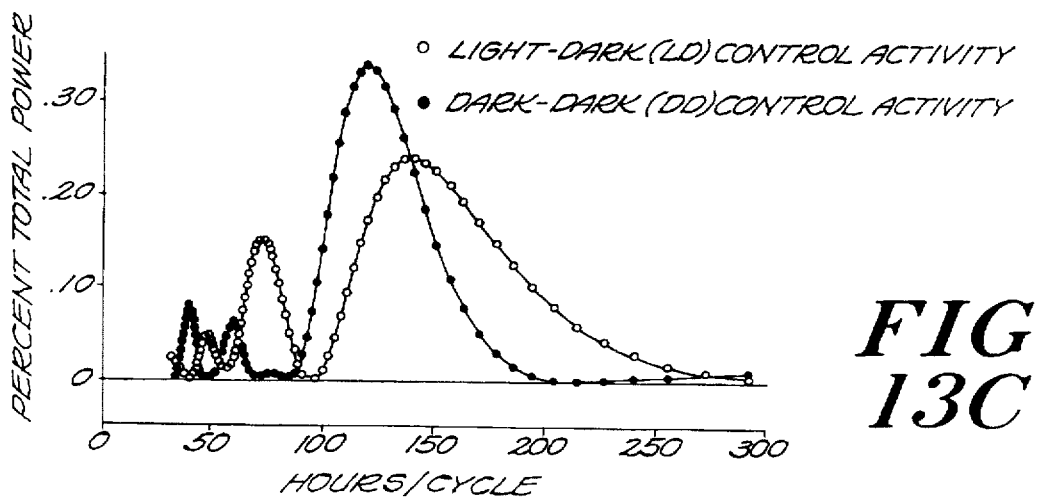
Figure 14A:
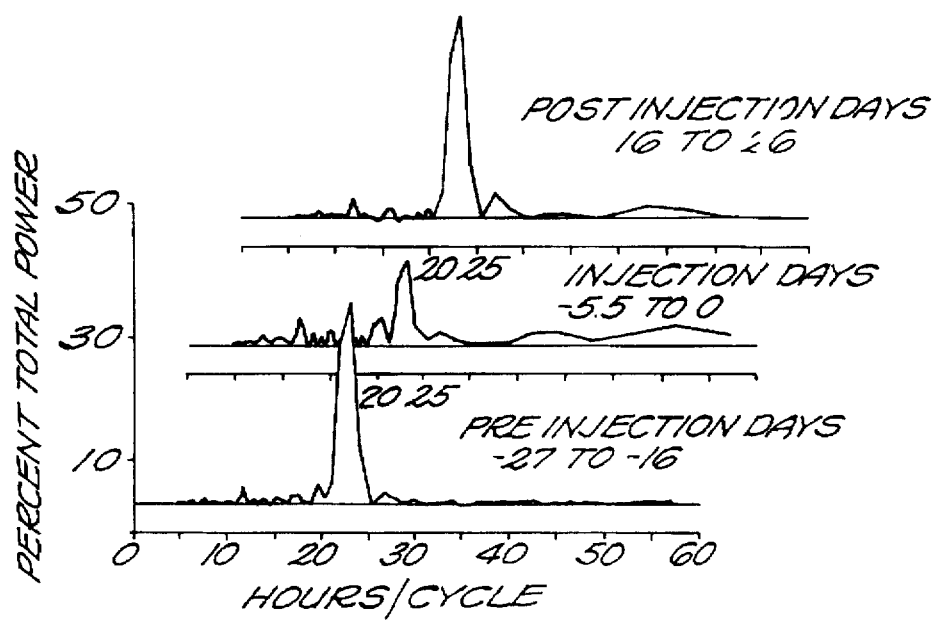
FIG. 14 shows a high resolution power spectra for control and MPTP mice.
Figure 14B:
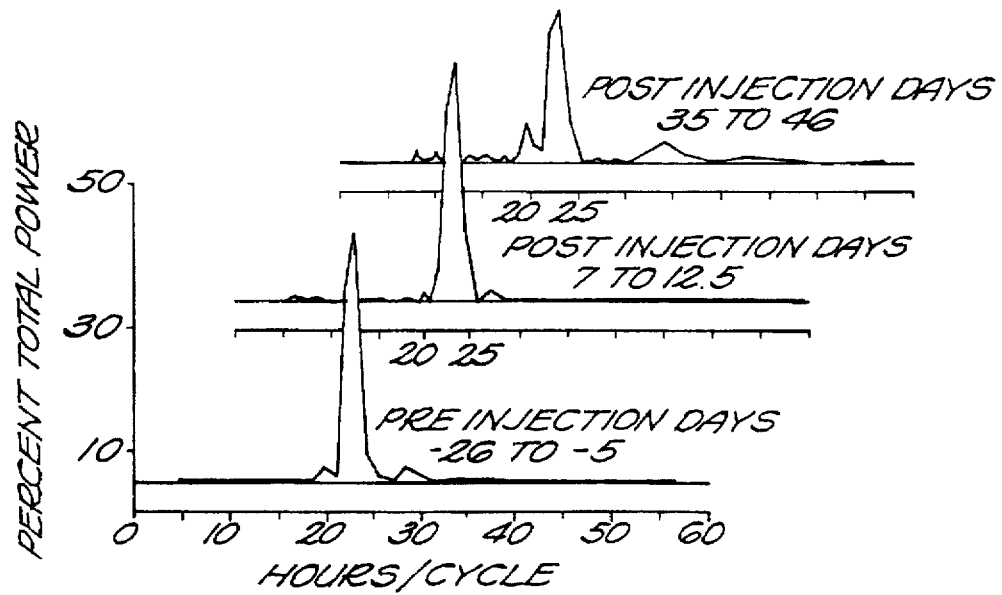
Figure 14C:
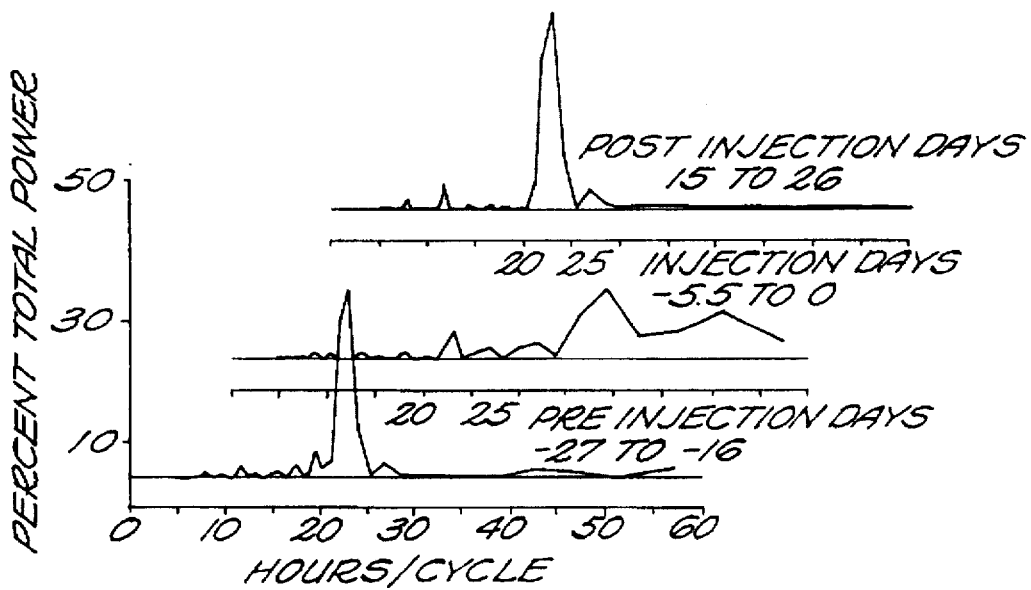
Figure 14D:
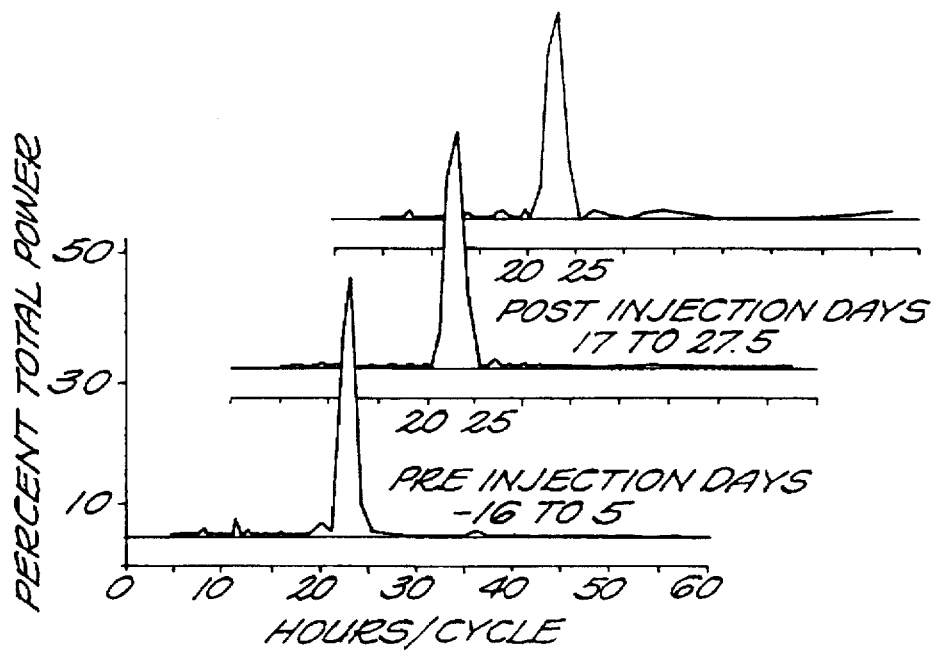

Analysis of the locomotory activity in the time domain was complicated by the superimposition of multiple endogenous activity cycles so that Fourier analysis was used to quantitate the data. High resolution power spectra for LD and DD preinjection control periods from a saline injected mouse are shown in FIG. 13. The spectra were calculated for 256 activity counts then padded to 4096 values with zeros before the Fourier transform was applied. In FIG. 13A, both LD and DD spectra display a major peak at approximately 24 hours/cycle which includes in excess of 75% of total power. Note the slight shift in the centroid of the DD peak to a cycle length which is approximately 9 minutes shorter than the LD peak. In FIG. 13B a secondary peak occurs between 100–250 hours/cycle which is consistent with previous observations from the raw data of FIG. 12. This peak is shifted by about 50 hours/cycle for the DD spectra as compared to the LD spectra. Longer hours/cycle values did not reveal any other peaks. Note that a third smaller peak arising only during LD entrainment occurs over 60–90 hours/cycle. The clear separation of the circadian peak from the slower peaks made it possible to independently evaluate the changes in the power of the dominant 24 hour component after MPTP treatment. The locomotory activity was therefore measured as the percentage power under the 22–26 hours/cycle peak.

In FIG. 14, panel A shows that interruption of the animals' endogenous activity by saline injections was sufficient to reduce the percentage power of the P22-26 relative to pre-injection and post-injection days. Hence, activity changes like those in Panel B could not be reliably interpreted for the MPTP injection period. Saline injections did not produce any changes in the P22-26 in the post-injection period (Panel C for an example). In contrast, the 150 and 300 mg/kg doses (see FIG. 15) resulted in marked depression of the P22-26 which recovered by days 12 to 20 (Panels B and D).

Figure 15:
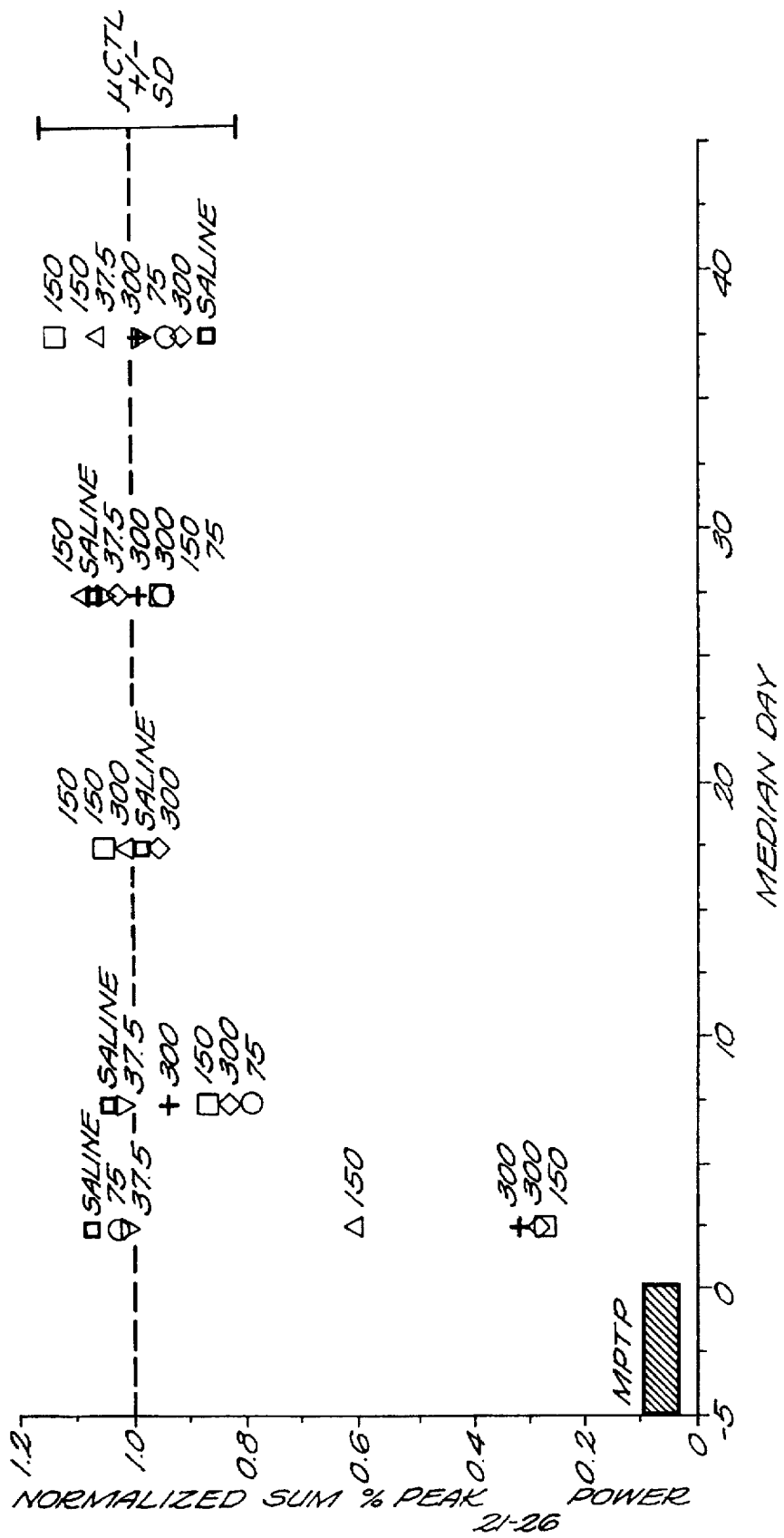
FIG. 15 is a graph showing the normalized sum % peak power versus median day.

FIG. 15 shows that saline and 37.5 or 75 mg/kg MPTP injections did not alter P22-26 locomotory activity significantly from that of the control pre-injection days (the error bar represents ±1 s.d. for the pooled control activity). In contrast, peak power for the P22-26 was reduced to 20–60% of mean control values in the 5 days following 150 or 300 mg/kg MPTP treatment and returned to normal by median Day 20.

Figure 16A:
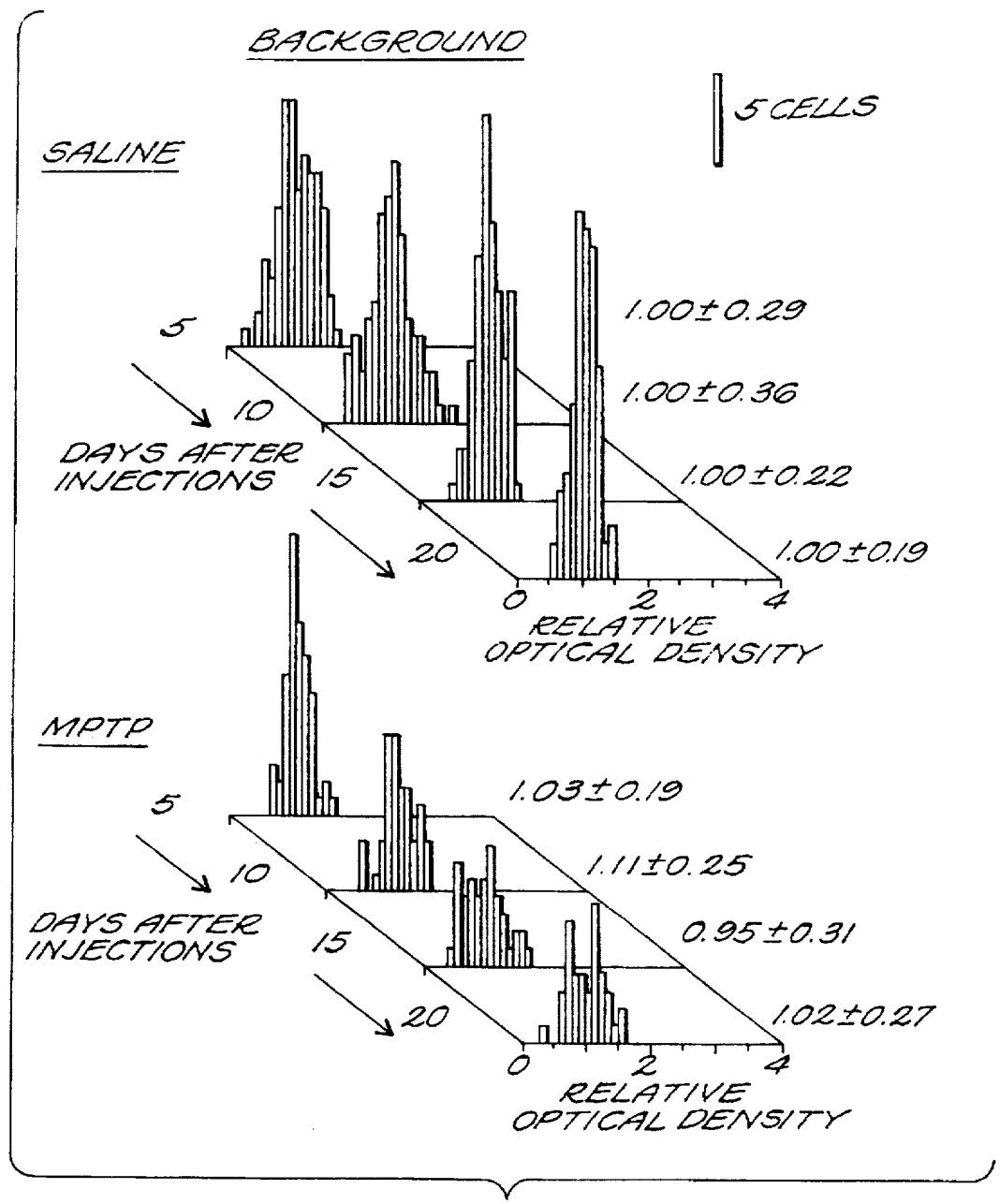
FIG. 16A and 16B show SNc sections for glued brains from animals treated with MPTP or saline.
Figure 16B:
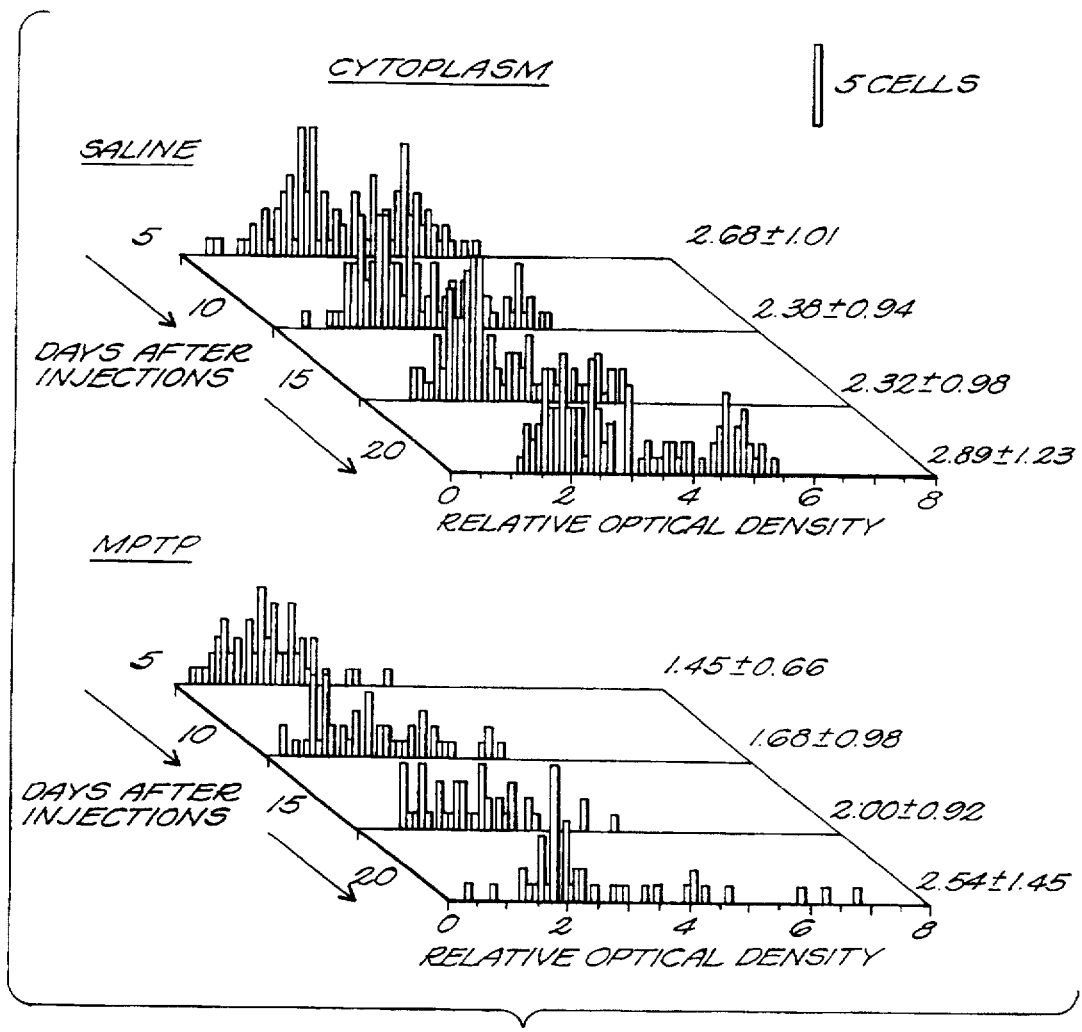
Figure 17A:
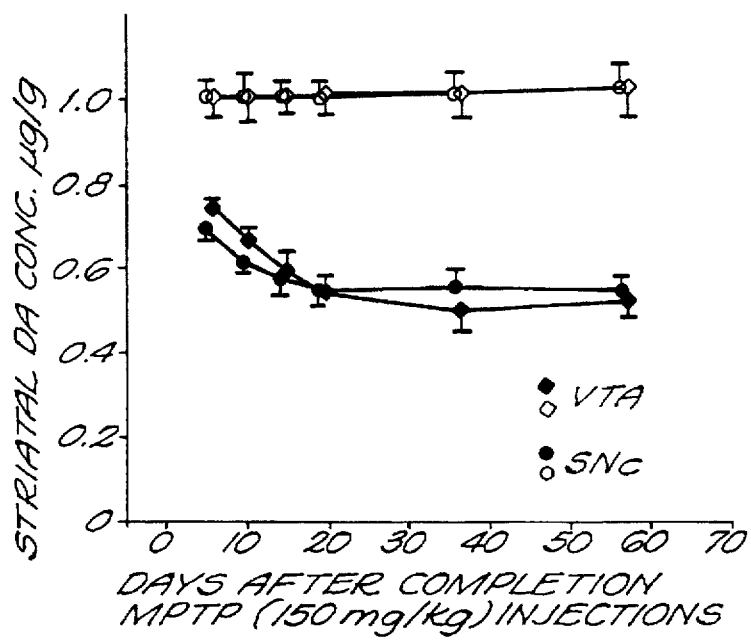
FIG. 17A, B, C, and D are graphs showing the counts of TH+ SNc and VTA neuronal somata following MPTP treatment taken through whole nuclei expressed as a percentage of the mean counts for the corresponding saline-injected animals (A); the concentration of striatal DA (B); the concentration of striatal DOPAC, and the DOPAC/DA ratio (D) for saline and MPTP injected mice.
Figure 17B:
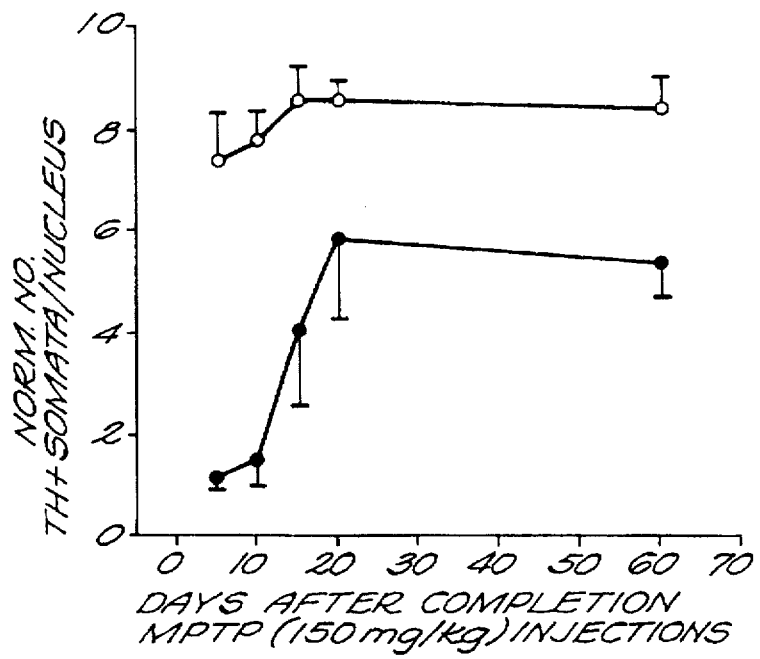
Figure 17C:
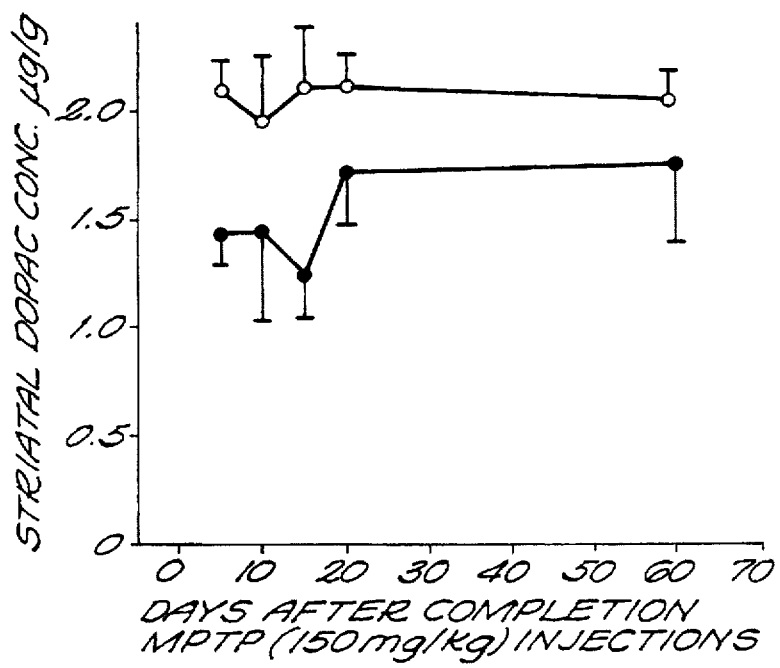
Figure 17D:
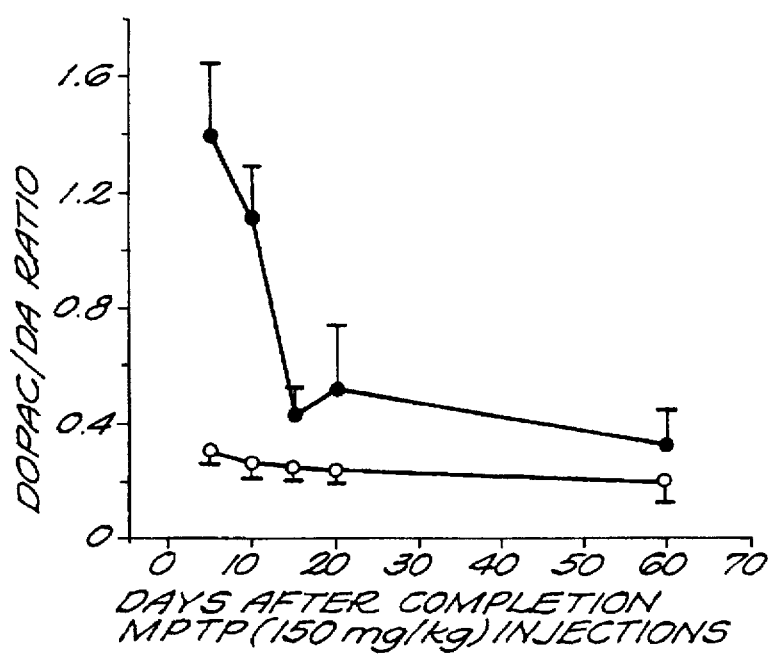

A second series of animals, treated with 150 mg/kg MPTP or saline, were sacrificed for TH immunocytochemistry and sections were visualized with avidin-conjugated horseradish peroxidase and diaminobenzidine at days 5, 10, 15, 20 and 60 following MPTP injection. The paraformaldehyde perfused brains were bisected along the midline and halves from a saline-injected and an MPTP-injected animal were glued together using Tissue-Tek so that surface landmarks were longitudinally in register. Serial 10 μm sections were taken through the brainstem to encompass an SNc from both animals so that SNc neurons from the saline and MPTP animals were immediately adjacent and were exposed to similar concentrations of the antibodies and reagents. Panel A and Panel B (FIG. 16) present SNc sections for glued brains at Days 5 and 20.

FIG. 17, Panel A presents the counts of TH+ SNc and VTA neuronal somata following MPTP treatment taken through whole nuclei expressed as a percentage of the mean counts for the corresponding saline-injected animals (error bars are s.d.). MPTP injected animals are represented by the filled symbols. Note the gradual decrease in the number of SNc somata with detectable TH immunoreactivity from Days 5 to 20 with an apparent maintenance of the number of TH+ somata after Day 20. Panels B, C and D present the concentration of striatal DA and DOPAC for the saline and MPTP injected animals. Note the similarity of the time course for the recovery of striatal DA concentrations toward normal levels with recovery of locomotory activity in FIG. 15. The DOPAC/DA ratio shows a marked increase and rapid decline over Days 5–10 for the MPTP injected animals and then maintains a constant Level at about 2 times that of the saline injected animals.

A computer optical density (OD) system was used to measure somal cytoplasmic TH immunoreactivity and the background immunoreactivity in the immediately adjacent tissue for randomly chosen SNc and VTA somata (Tatton, W. G. et al. Brain Res. 1990, 527, 21–32) for the glued brain sections. Background OD per unit area was subtracted from somal OD per unit area for each cell to obtain an estimate of cytoplasmic TH immunodensity per unit area. The mean background OD for the saline injected half of each glued section was used to normalize the values for the MPTP background OD and the saline and MPTP cytoplasmic ODs. FIG. 17 presents distributions for the normalized background and cytoplasmic measurements for TH+ SNc somata at Days 5–20 after saline or 150 mg/kg MPTP injections. In this and other studies using the glued brains, background values did not differ significantly (p<0.05) for the saline injected and MPTP injected halves thereby allowing valid comparisons of the cytoplasmic values. The control distributions for the saline injected animals often revealed a bimodal distribution of TH immunodensity for the SNc somata ranging from 0.5 to 6 times mean background levels with modes at about 2 and 4 times mean background level.

Figure 18A:
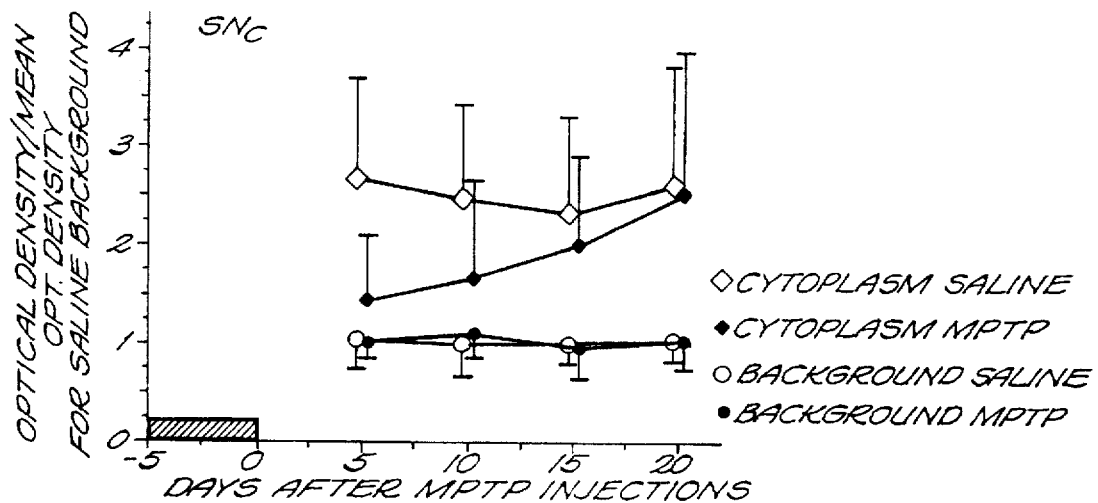
FIG. 18 is a graph showing the mean OD/mean O.D. for saline background versus days after MPTP injections.
Figure 18B:
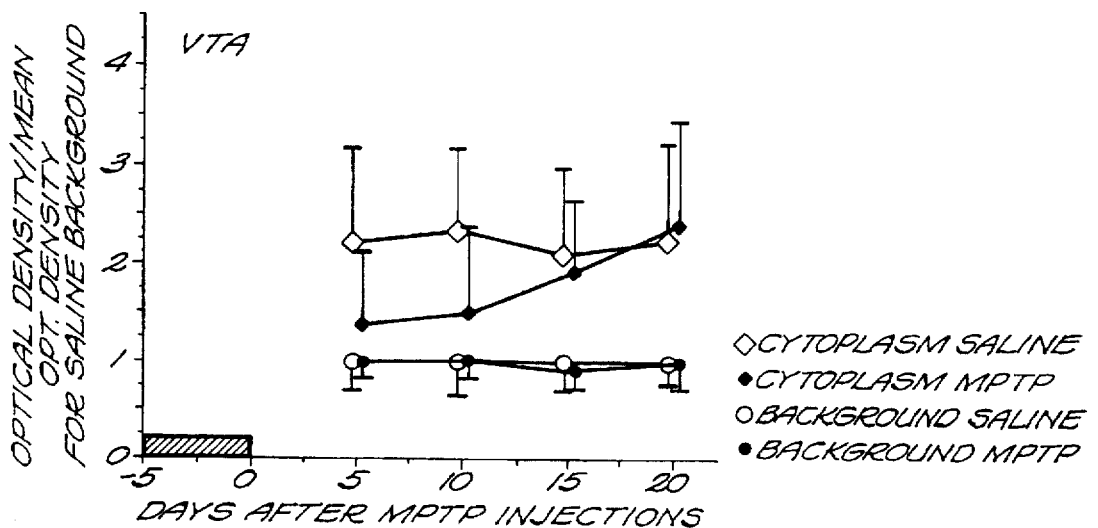
Figures 1, 19A:
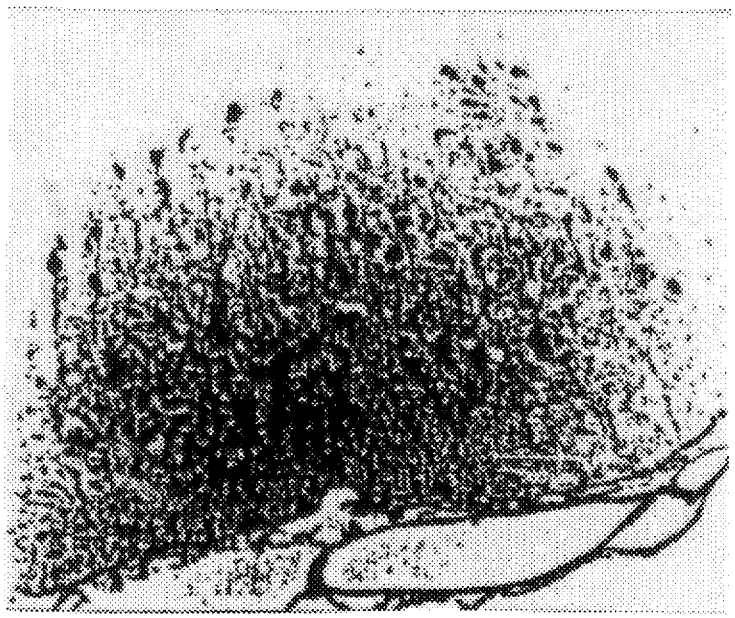
Figures 2, 19A:
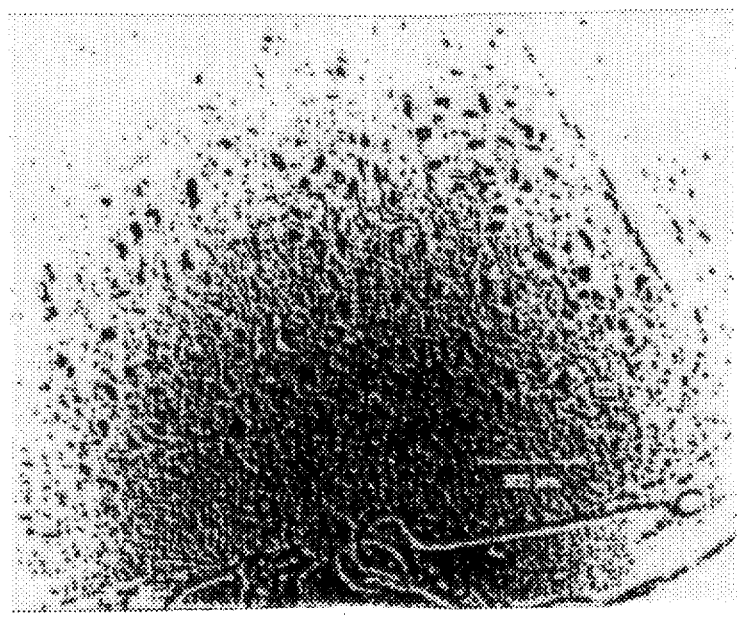
Figures 1, 19B:
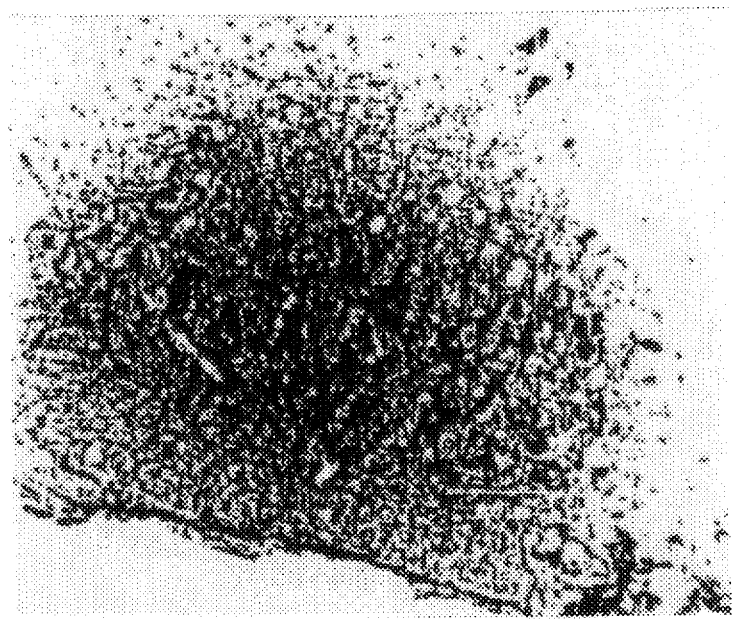
Figures 2, 19B:
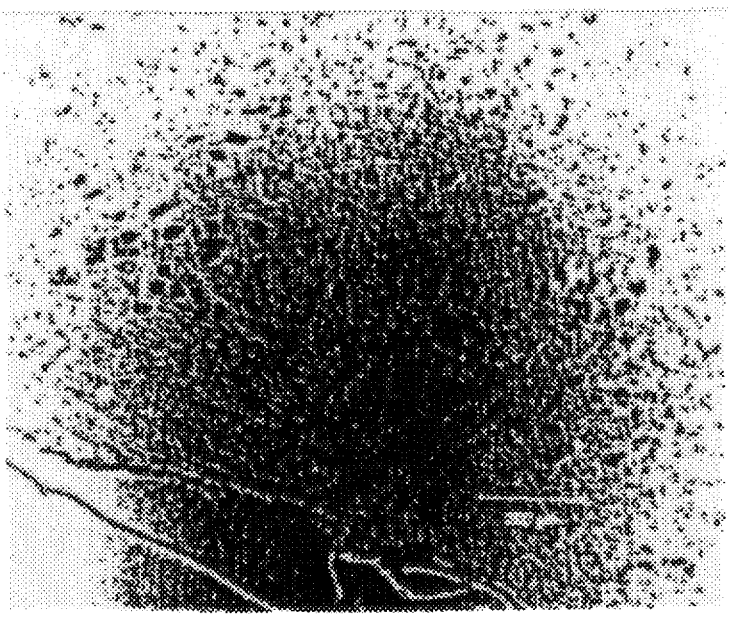

Within 5 days there was a marked reduction in cytoplasmic TH immunodensity for the MPTP treated SNc and VTA somata with a gradual recovery to a distribution approximately that of the saline controls by 20 days post-injection (FIGS. 17 and 18). The recovery of the TH immunodensity of SNc and VTA neurons following MPTP treatment parallels the recovery of striatal DA concentrations and locomotory activity.

The inventors have adapted spectral analysis techniques with fast Fourier transforms to the analysis of long term locomotory activity in mice treated with MPTP. This provides both highly sensitive and reproducible data that is not dependent on subjective assessment of animals that have been aroused by recent handling or the presence of observers. Initially, it was proposed that MPTP did not produce motor deficits in rodents due to the view that rat and mouse SNc neurons were resistant to the toxin. This was based largely on neurochemical data that reported only transient changes in striatal dopamine following MPTP (Ricuarte, G. A. et al. Brain Res. 1986, 376, 117–124, and Walters, A., et al. Biogenic Amines 1984, 1, 297–302). Others reported slowed limb movements, abnormal gait and chronically reduced locomotory activity in mice treated with high doses of the toxin which appeared to correlate with maintained changes in striatal DA concentration (Duvoisin, R. C., et al. In Recent Development in Parkinson's Disease; S. Fahn et al. Raven Press: New York, 1986; p. 147–154, Heikkila, R. E., et al. Science 1984, 224, 1451–1453, Heikkila, R. E., et al. Life Sci. 1985, 36, 231–236). Previous measurements of changes in locomotory activity in rodents following MPTP unfortunately have been either short term (Saghal A., et al. Neurosci. Lett. 1985, 48, 179–184) or brief isolated measurements (Willis, G. L., et al. Brain Res Bull 1987, 19, 57–62). To date there has been no satisfactory explanation of the behavioral recovery observed in various MPTP models including the cat (Schneider, J. S., eta la. Exp Neurol 1986, 91, 293–307), the marmoset (Waters, C. M., et al. Neuroscience 1987, 23, 1025–1039) or the rodent (Chiueh, C. C., et al. Psychopharmacol. Bull. 1984, 20, 548–553, and Johannessen, J. M. et al. Life Sci. 1985, 36, 219–224).

Locomotory activity as measured by the power under the P22-26 peak, striatal DA concentration and TH immunodensity in SNc and VTA somata are correlated in their recovery toward normal after MPTP treatment. The numbers of SNc and VTA somata with detectable TH immunoreactivity decay to a steady state level over the first 20 days after MPTP treatment. Hence dopamine content in the striatum is increasing while the number of SNc and VTA neurons with detectable TH content is decreasing. The rapid rise and fall of the DOPAC/DA ratio likely is related to the death of DA terminals in the striatum with loss of DA into the extracellular space. Yet the ratio is maintained at an increased level after Day 15 in support of the earlier findings suggesting that DA synthesis is increased in SNc neurons surviving MPTP exposure.

The measurements of TH immunodensity in the somata of SNc and VTA neurons are unlikely to provide a linear estimate of TH concentration. Although the use of the peroxidase reaction likely provides a linear estimate of the numbers of the secondary antibody-avidin complexes in the cytoplasm (Reis, D. J., et al. In Cytochemical Methods in Neuroanatomy Alan R. Liss, Inc.: New York, 1982; p. 205–228), the affinity constants for the inventors' polyclonal antibodies and those for the immunoreaction between the primary and secondary antibodies may not provide for a linear relationship between the concentration of the epitope and the concentration of avidin molecules. Yet, the results probably do indicate a recovery in TH concentrations in the somata of VTA and SNc surviving MPTP exposure. The recovery of TH immunodensity parallels the increases in striatal DA content which suggests that a recovery of TH synthesis is a factor in the recovery of DA content and possibly increased DA synthesis by individual surviving neurons.

Neostriatal dopaminergic and other ctecholaminergic systems in rodents have been related to the generation of locomotory activity (Tabar J., et al. Pharmacol Biochem Behav 1989, 33, 139–146, Oberlander, C., et al. Neurosci. Lett. 1986, 67, 113–118, Melnick, M. E. et al. 17th Annual Meeting Of The Society For Neuroscience, New Orleans, La., USA, November 1987, 13, Marek, G. J., et al. Brain Res 1990, 517, 1–7, Kostowski, W., et al. Acta Physiol. Pol. 1982, 33, 385–388, Fink, J. S., Smith, G. P. J. Comp. Physiol. Psych. 1979, 93, 24–65). Yet the specific role, if any, of SNc or VTA neurons is uncertain. Hence the correlated recoveries for SNc and striatal parameters relative to the locomotory activity do not necessarily imply cause and effect. Yet the present inventors have suggested that since MPTP causes similar loss of TH+ neurons in a variety of catecholaminergic systems (Seniuk, N. A. et al. Brain Res. 1990, 527: p.7–20), similar recovery of transmitter-related function in those systems to that we have shown for SNc and VTA dopaminergic neurons (Seniuk, N. A. et al. Brain Res. 1990, 527: p.7–20) may underlie the behavioral recovery. The recovery of DA synthesis may represent an attempt of the SNc neurons surviving the MPTP exposure to compensate for the loss of their fellows an that a component of the compensation is related to a recovery and then increased synthesis of tyrosine hydroxylase in the neurons surviving the MPTP exposure.

Example 4

An experiment was carried out to determine whether deprenyl can reduce the death of other axonally-damaged neuronal phenotypes e.g. rat motoneurons. The proportion of rat motoneurons which die after axotomy is maximal during the first 4 days of life (80–90% loss) and then diminishes to adult levels (20–30% loss) over the next 3 to 4 weeks (Sendtner et al. Nature, 345, 440–441, 1990, Snider W. D. and Thanedar, S. J. Compl. Neuro 1, 270,489, 1989). Two groups (n=6) of fourteen day old rats received a unilateral facial nerve transection (lesion) while two groups were unlesioned (no lesion). Paired lesion and no lesion groups were treated with saline, deprenyl (0.01 and 10 mg/kg), pargyline (10 mg/kg) every other day. The rats were sacrificed at 21 days after axotomy and serial coronal histological sections of the brainstem at the level of the facial nuclei processed for choline acetyl transferase (ChAT) immunocytochemistry (Tatton et al, Brain Res. 527:21, 1990 which is incorporated herein by reference) and Nissl staining (Seniuk et al., Brain Res. 527: 7, 1990; Tatton et al. Brain Res. 527:21, 1990 which are incorporated herein by reference) (FIG. 19).

In particular, the right facial nerves were transected at their exits for the stylomastoid foramen under halothane-nitrous oxide anaesthesia for two groups of 14 day old Sprague-Dawley rats while two other groups were unoperated (n=6 in each group). On the day of the surgery, a lesioned and an unlesioned group were begun on deprenyl 10 mg/kg intraperitoneally every second day until sacrifice. The other lesioned and unlesioned groups were given identical injections with saline. Twenty one days after the transections, the rats were killed by anaesthetic overdose followed by perfusion with isotonic saline and 4% paraformaldehyde in phosphate buffer. Brains from the unlesioned groups were bisected longitudinally along the midline and the half brains from saline treated and deprenyl treated animals were glued together using Tissue-Tek so that the surface landmarks coincided. The glued brains for the unlesioned animals and the intact brains for the lesioned animals were frozen in −70° C. methylbutane and 10 µm serial sections were cut through the portion of the medulla containing the facial nuclei. Every third serial section was reacted with a polyclonal antibody against ChAT then incubated with biotinylated secondary antibody, followed by incubation with HRP conjugated avidin and finally reacted with diaminobenzidine and $H_2O_2$ (Tatton et al., Brain Res. 527:21, 1990). The paired sections for the glued half brains insured that any differences in immunoreaction between the deprenyl and saline unlesioned control groups were not due to different penetration or exposure to the antibodies or the reagents.

The following experiments were also carried out using the procedures described above:

A group of fourteen day old rats received a unilateral facial nerve transection (lesion) while groups were unlesioned (no lesion). Paired lesion and no lesion groups were treated with saline or deprenyl (10 mg/kg) every other day. The rats were sacrificed as and ChAT immunochemistry was carried out as described herein.

A group of fourteen day old rats received a unilateral facial nerve transection and were treated with 10 mg/kg deprenyl every other day for 21 days. Animals were sacrificed at 35 days of age and at 65 days of age and ChAT immunochemistry was carried out as described herein.

A group of one day old rats received a unilateral facial nerve transection and were treated with deprenyl every other day with saline or deprenyl (10 mg/kg). The animals were sacrificed at 8 days of age and ChAT immunochemistry was carried out as described herein.

FIG. 19 shows photomicrographs of adjacent ChAT immunoreacted (A1 and B1) and Nissl stained (A2 and B2) sections through the facial nucleus ipsilateral to transection of the facial nerve. A1 and A2 are for saline treated animals and B1 and B2 are for deprenyl treated animals.

Figure 20:
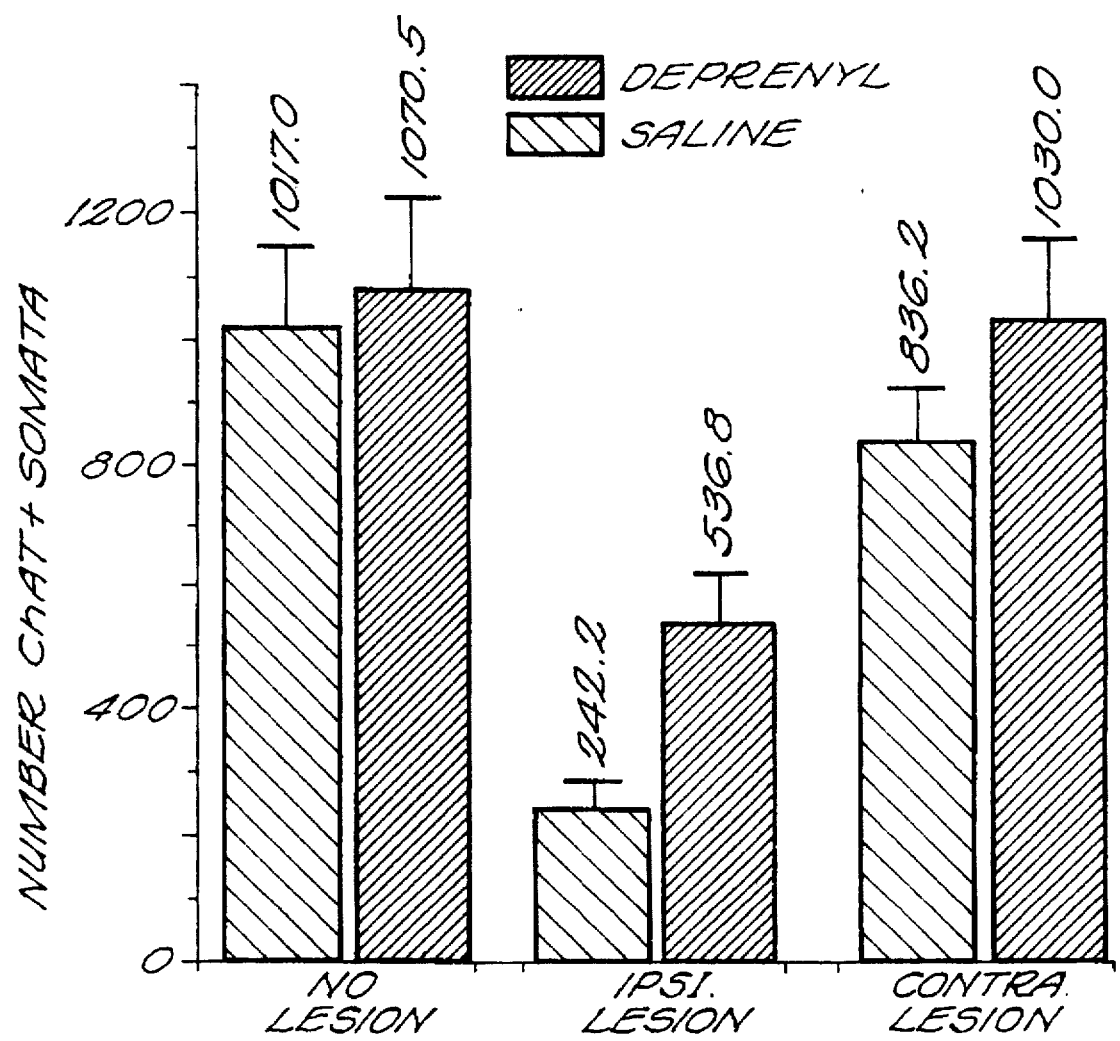
FIG. 20 is a bar graph for the counts of ChAT+ somata for the facial nuclei for the different lesion and treatment groups (bars-means, error bars—standard deviations)

FIG. 20 is a bar graph for the counts of ChAT+ somata for the facial nuclei for the different lesion and treatment groups (bars-means, error bars—standard deviations). ChAT immunoreactive somata containing nuclear profiles were counted from every third section taken serially through entire facial nuclei. The value at the top of each bar is the mean. The Ipsi.Lesion and Contra.Lesion indicate the nuclei located ipsilaterally and contralaterally to the facial nerve transection respectively. The counts were not adjusted to estimate the total numbers of ChAT+ somata in the facial nuclei, so the numbers for unlesioned groups are approximately one third of values reported for counts of Nissl stained somata. The values were compared statistically in a pairwise fashion using the Mann Whitney U test.

As shown in FIG. 20 counts of ChAT immunopositive (ChAT+) somata for every third serial section through the full lengths of the facial nuclei were statistically the same (p=0.520) for the no lesion-saline and the no lesion-deprenyl groups. In contrast, the numbers of ChAT+ somata decreased significantly for the lesion-saline group for the facial nuclei both ipsilateral (23.8% no lesion-saline, p=0.003) and contralateral (82.2% no lesion-saline, p=0.024) to the facial nerve transection. Deprenyl treatment more than doubled the number of ChAT+ somata for the ipsilateral lesioned facial nucleus (52.7% no lesion-saline p=0.004) and prevented the decrease in the ChAT+ counts for the contralateral nucleus so that they were statistically the same as the no lesion groups (p=0.873).

Figure 21A:
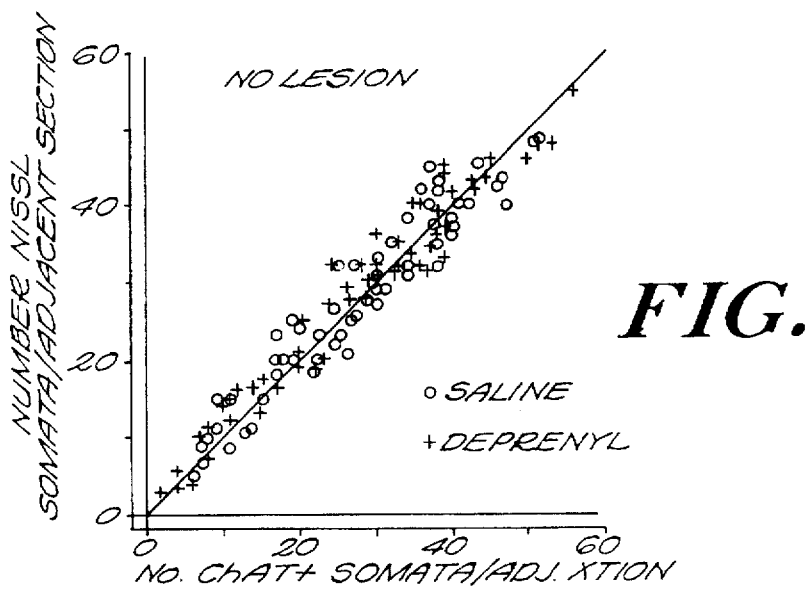
FIG. 21 are graphs showing joint Nissl/ChAT+ counts of adjacent sections for the no lesion groups (FIG. 14A), the ipsilateral lesion-saline animals (FIG. 14B), the lesion-deprenyl animals (FIG. 14B), and the contralateral lesion animals (FIG. 14C)
Figure 21B:
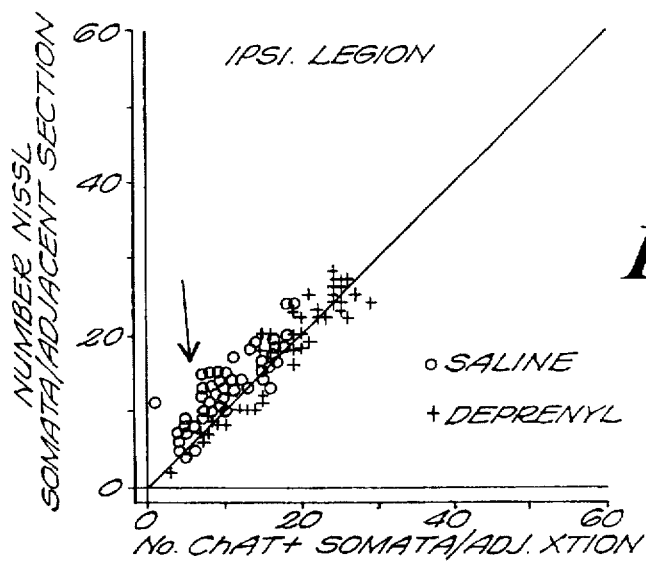
Figure 21C:
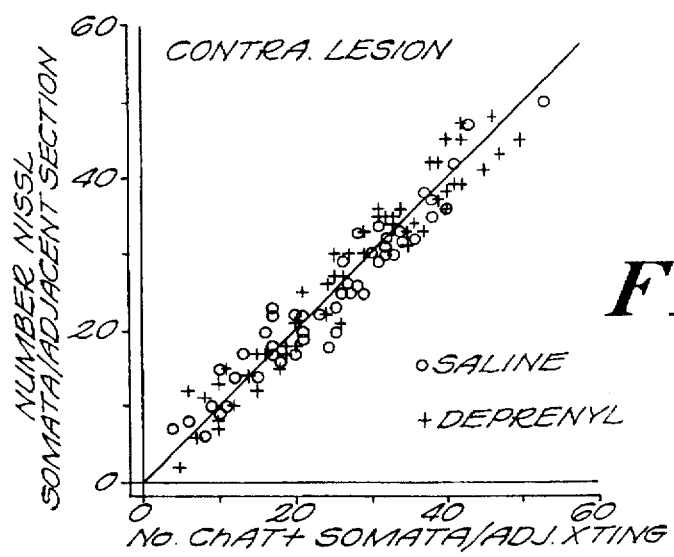

FIG. 21 shows the joint Nissl/ChAT+ counts of adjacent sections. One of each pair of intervening sections between those that were immunoreacted for ChAT was Nissl stained. With the aid of a camera lucida the number of ChAT+ somata and Nissl-stained nucleolus-containing somata (Oppenheim, R. W. J. Comp. Neurol. 246:281, 1986 for criteria) were counted in matching areas of adjacent sections on 20 randomly-chosen sections through the length of each nucleus for each animal. Nissl counts were then plotted against ChAT+ counts for the adjacent sections (values from three animals in each lesion-treatment group were pooled). Comparison of Nissl and ChAT+ somal counts were done to determine whether decreases in the number of immunopositive somata reflected the death of the motoneurons or loss of immunoreactivity.

The joint plots of the Nissl/ChAT somal counts for the no lesion groups (FIG. 21) show distributions that are symmetrical around the equal value diagonal with similar means and standard deviations for the saline (Nissl 27.6±12.04, ChAT+ 27.3±13.80, p=0.526, Nissl and ChAT counts for the same groups were compared using the paired t test) and deprenyl groups (Nissl 28.9±13.2, ChAT 28.5+/13.8, p=0.641). The ipsilateral lesion-saline animals (FIG. 21) show lower joint values with an asymmetrical distribution with respect to the equal value diagonal (the shift to higher Nissl values is marked by an arrow) with is reflected in the higher mean value for the Nissl counts (12.6±4.18) relative to the ChAT+ counts (9.7±4.0, p=0.001). The lesion-deprenyl points (FIG. 21B) showed a smaller reduction than the saline points and had a symmetrical distribution around the equivalent value diagonal (Nissl 17.6±±6.5, ChAT+ 17.5±6.1, p=0.616). Finally, the plot for the contralateral lesion animals (FIG. 21C) shows that the points for both the saline (Nissl 24.6±10.1, ChAT+ 24.8±10.7, p=0.159) and deprenyl (Nissl 28.9±12.1, 28.5±12.0, p=0.741) groups are symmetrically distributed relative to the equivalent value diagonal.

Thus, the distribution of the joint Nissl/ChAT+ plots to above the equal value diagonal and the significant difference between the joint Nissl and ChAT+ counts for the ipsilateral lesion-saline animals (FIG. 21) showed that about 84% of the decrease in the numbers of ChAT+ somata shown in FIG. 20 resulted from motoneuronal death while loss of ChAT immunoreactivity only caused about 16% of the decrease in ChAT+ motoneurons. The joint counts also showed that all of the loss of ChAT+ somata from the contralateral nuclei resulted from motoneuronal death. Most importantly, the joint counts established that deprenyl treatment caused a marked reduction in the motoneuronal death and reversed or prevented the loss of ChAT immunoreactivity in surviving motoneurons in the ipsilateral nuclei. It also prevented any motoneuronal death in the contralateral nuclei.

Figures 1, 22B:
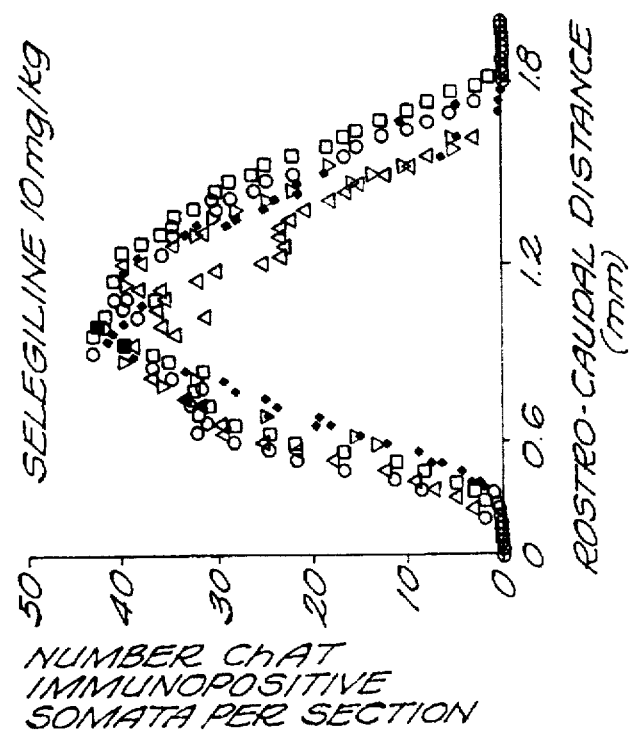
Figures 1, 22A:
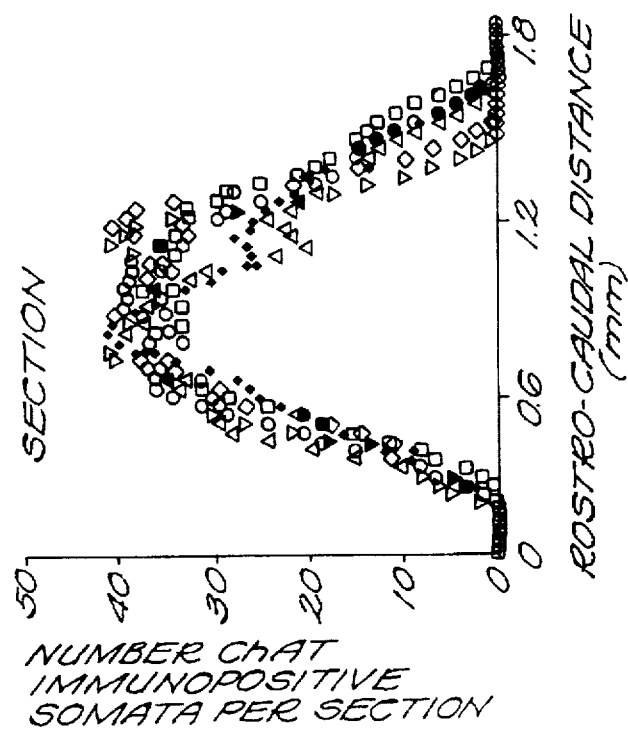

FIG. 22 shows Chat+ counts for facial motoneurons in 35 day old rats after a unilateral axotomy at 14 days of age. It shows the rescue of the motoneurons whose axons were transected (IPSI transection) and the complementary rescue of the small number of facial motoneurons that die on the opposite side of the brainstem (Contra transection).

Figure 23:
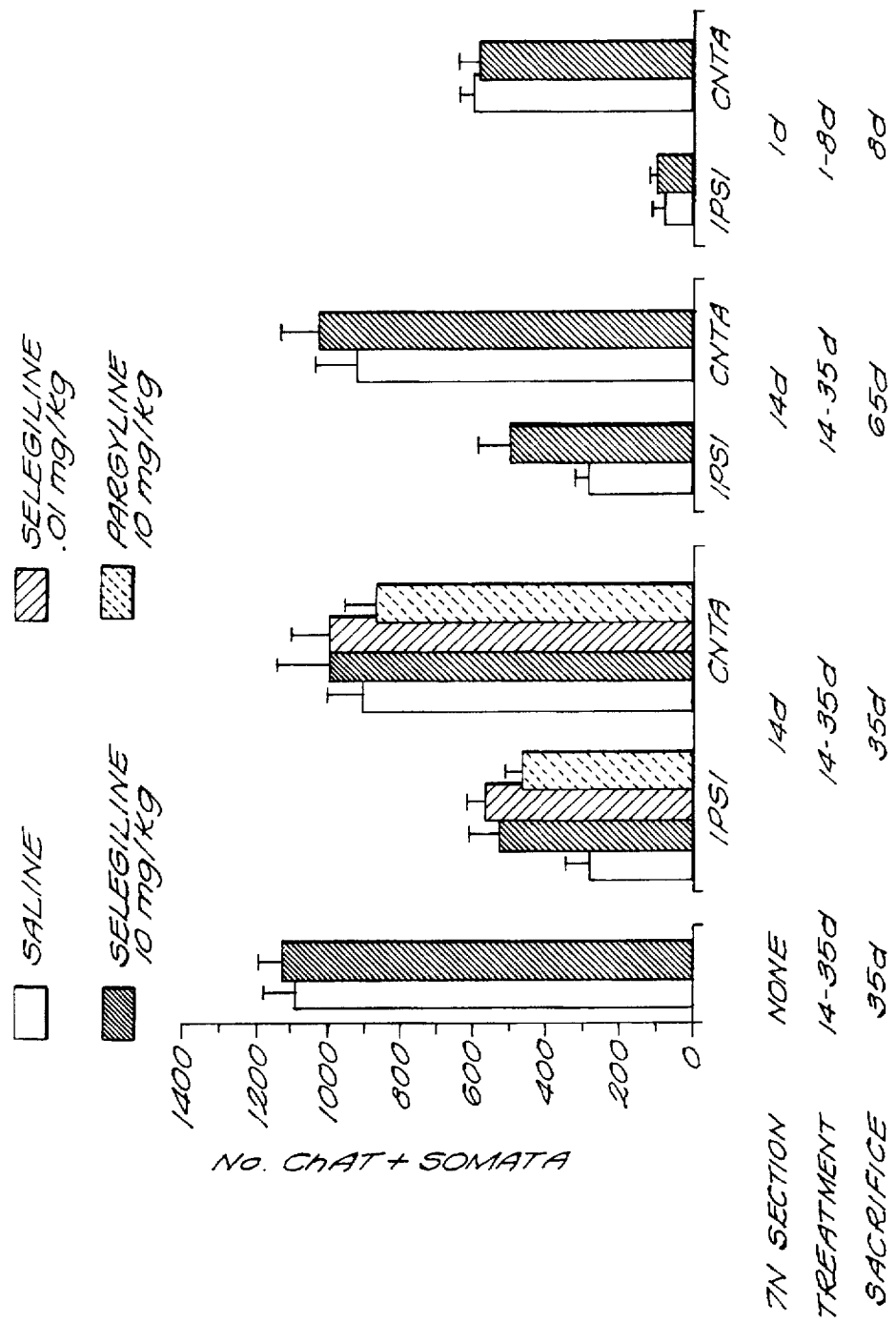
FIG. 23 shows the data shown in FIG. 20 and includes data for additional animals.

FIG. 23 sets out the data shown in FIG. 20 (leftmost two groups of bars) and includes data from some additional animals (group sizes increased from 6 to 8 or more). It also shows that pargyline rescues the motoneurons (hatched bars, possibly more weakly than deprenyl as the groups differ at the p<0.05 level). Further, a dose of 0.01 mg/kg of deprenyl was found to be just as effective as 10 mg/kg deprenyl in rescuing the motoneurons similar to the 0.01 mg/kg dose used with the MPTP model.

Animals lesioned at 14 days, treated for the next 21 days with 10 mg/kg deprenyl (d14–35) and then left untreated until 65 days of age do not show any further motoneuronal death (compare the third group of bars from the left to the corresponding bars in the second group that were sacrificed at 35 days of age when deprenyl treatment was still under way). This indicates that the rescue is permanent for the axotomized motoneuron i.e. the motoneurons do not begin to die when deprenyl treatment is discontinued after 21 days and there is not further death over the next 30 days.

FIG. 23 also shows that rat motoneurons whose axons are transected at 1 day of age have a greater amount of death than 14 day motoneurons and cannot be rescued by deprenyl. Therefore, it appears that some factor must reach maturity in the nervous system before deprenyl can be effective and that factor appears between 1 and 14 days of age.

This is the first evidence that deprenyl can prevent the death of motoneurons and is consistent with the work indicating that deprenyl can reduce the death of axonally-damaged neurons. The death of axotomized motoneurons in immature rats is believed to reflect a dependency of the motoneurons for trophic support from the muscles they innervate (Crews, L. and Wigston, D. J.; J. Neurosci 10, 1643, 1990; Snider, W>D. and Thanedar, S. supra). Recent studies have shown that some neuronotrophic factors can reduce the loss of the motoneurons supporting that concept (Sendtner, M. et al, Nature 345,440, 1990). This study suggests that deprenyl has the capacity to activate some mechanism which compensates for the loss of target derived trophic agents. Part of the action of deprenyl in neurodegenerative diseases may reflect a similar compensation for reduced trophic support.

The finding of a small amount of motoneuronal death in the facial nucleus contralateral to a facial nerve transection is in accord with previous reports of decreased numbers of axons in the intact nerve contralateral to the transection of a motor nerve (Tamaki K. Anat. Rec. 56, 219, 1933) and a variety of other changes in contralateral nuclei (Pearson, C. A. et al. Brain Res. 463, 1988). Deprenyl completely prevents the death of the contralateral motoneurons.

Axotomy initiates transient changes in protein synthesis in facial motoneurons (Tetzlaff, W. et al. Neuro Sci. 8, 3191 (1988)) which include a decrease in choline acetyl transferase (Hoeover, D. R. & Hancock, J. C. Neuroscience 15, 481, 1985). The small proportion of saline-treated motoneurons in the ipsilateral nuclei (16%) which lost ChAT immunoreactivity probably reflects the surviving motoneurons that had not recovered sufficient ChAT concentrations to be immunochemically detectable. Deprenyl prevented or reversed the loss of ChAT immunoreactivity in surviving motoneurons.

The dose of deprenyl (10 mg/kg) was sufficient to block the majority of MAO-B activity and some MAO-A activity as well (Demarest, K. T., Aazzaro, A. J. in Monoamine Oxidase: Structure, Function and Altered Functions (eds. Singer, T. P., Korff, R. W. and Murphy, D. L.) 423–340, Academic Press, New York, 1979) hence the reduction in motoneuron death may be due to MAO-B or MAO-A inhibition or may be independent of both enzymes. However, it is expected that a 0.01 mg/kg deprenyl dose will produce a reduction in motoneuron death similar to that obtained with the 10 mg/kg dose. The 0.01 mg/kg dose does not produce any significant MAO-A or MAO-B inhibition indicating that the rescue with 0.01 mg/dg deprenyl is not due to MAO-A or MAO-B inhibition.(See example 2) Thus, it is more likely that the reduction in motoneuron death will be independent of MAO-B or MAO-A.

A recent study has shown that MAO-inhibitors may be more effective then deprenyl in reducing the necrosis of dorsal striatal neurons after a transient interruption of the arterial blood supply to that region (Matsui, Y. and Kamagae, Y., Neurossci lett 126, 175–178, 1991). Yet deprenyl doses (0.25 mg/kg) too low to produce inhibition of MAO-A but sufficient to product 20–75% inhibition of MAO-B in mice are as effective as a 10 mg/kg dose in preventing the death of SNc neurons. MAO-B is largely concentrated in glial cells although present in some serotonergic and histaminergic neurons (Vincent, S. R. Neurosci 28, 189–199 (1989); Pintari, J. E. et al. Brain Res. 276, 127–140, 1983). Since microglial cells show a proliferative response and astroglia respond by an increase in protein synthesis to axotomy involving nearby motoneurons, glial cells may be involved in deprenyl-induced prevention of neuronal death.

Example 5

Age Related Death of Mouse SNC Neurons

Studies were carried out to determine whether deprenyl prevents age-related death of mouse dSNc neurons using the procedures set out in Tatton W. G. et al Neurobiol. Aging 1991; 12:5,543. The results are shown in FIG. 24.

Figure 24:
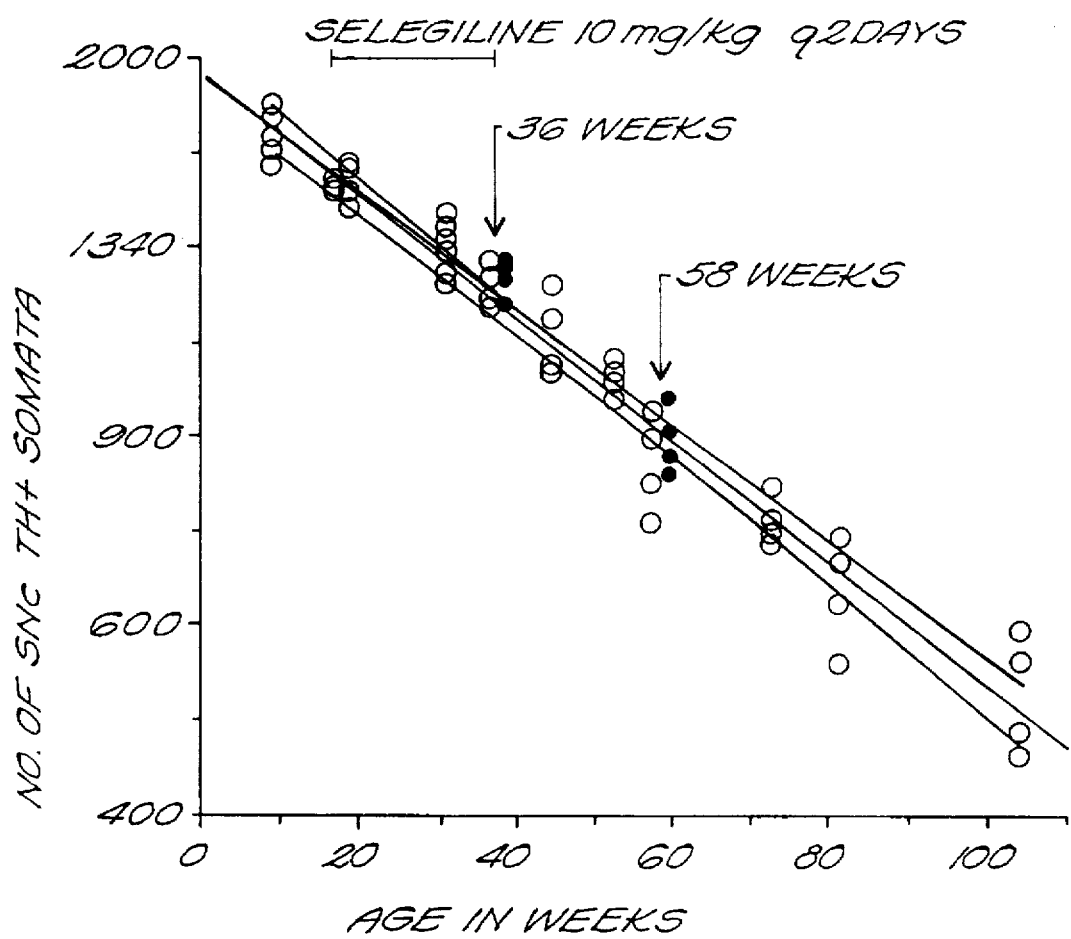
FIG. 24 shows the counts of TH+ SNc somata following treatment with deprenyl.

As shown in FIG. 24, deprenyl does not prevent age-related death of mouse DSN neurons.

Example 6

N-(2-aminoethyl)-4-chlorobenzamidehydrocloride having the following formula

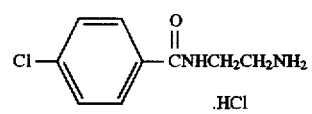

was obtained from Research Biochemicals Incorporated, Natick, Mass., U.S.A. (Cat. No. R-106, No. R016-6491) and was tested to determine if it rescued immature axotomized motoneurons. A group of fourteen day old rats received a unilateral facia nerve transection and were treated with 10.5 mg/Kg N-(2-aminoethyl)-4-chlorobenzamide every other day for 21 days. The rats were sacrified at 35 days of age and CHAT+ immunochemistry was carried out as described in Example 4.

Figure 25:
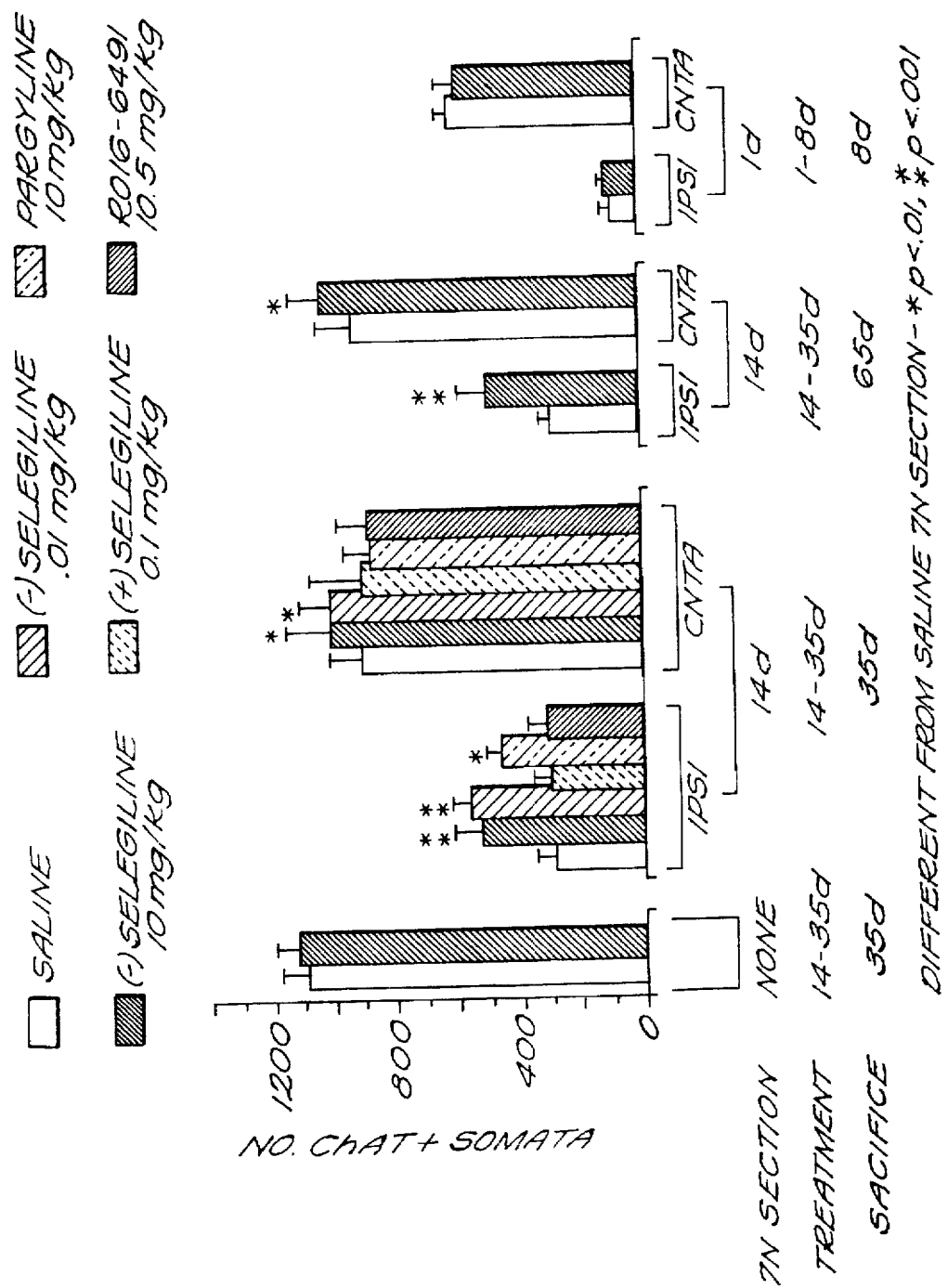
FIG. 25 shows the data shown in FIG. 23 and includes data from animals treated with N-(2-aminoethyl)-4-chlorobenzamide.

FIG. 25 contains the data shown in FIG. 23 and includes data from the animals treated with N-(2-aminoethyl)-4-chlorobenzamide.

As shown in FIG. 25 the compound did not rescue the immature axotomized motoneurons (FIG. 25). It should be noted that the compound does not have the triple bond C ending of the propargyl terminus of deprenyl and pargyline so that it attaches to a different part of the flavine portion of MAO-B. The propargyl attachment is permanent (irreversible inhibition of MAO-B) while the N-(2-aminoethyl)-4-chlorobenzamide attachment is reversible and short lived.

Example 7

The (+) isomer and (−) isomer of deprenyl were tested to determine whether the rescue of immature axotomized motoneurons was stereospecific. A group of fourteen day old rats received a unilateral facial nerve transection and were treated with 0.1 mg/Kg of the (−) isomer or (+) isomer of deprenyl every other day for 21 days. The rats were sacrificed at 35 days of age and CHAT+ immunochemistry was carried out as described in Example 4. As shown in FIG. 25, the (+) deprenyl at a dosage of 0.1 mg/Kg does not rescue the motoneurons. The rescue appears to be stereospecific to the (−) isomer. Thus, even through the (+) deprenyl has a terminal propargyl, the optical rotation relative to the phenol ring and the intermediate portions of the molecule may prevent attachment to the molecular site that initiates the rescue.

Example 8

Studies were carried out to determine the affect of deprenyl in an animal stroke model. Rats were treated with carbonmonoxide and received glucose i.v. The carotid artery was then clamped and deprenyl was administered to the animals. The clamp was then removed causing stroke in the animals. Deprenyl was also administered to a group of untreated animals one half hour after removal of the clamp. Positive neurons were determined in serial sections of the brain as described above. Deprenyl was found to reduce neuronal death and decreased the extent of damaged areas, in particular in the hippocampus.

We claim:

1. A method for rescuing damaged nerve cells in a patient, comprising:

administering to a patient in need thereof an amount of deprenyl, or a pharmaceutically acceptable salt thereof, such that rescuing of damaged nerve cells occurs in the patient for a condition in which the damaged nerve cells are sensitive to said deprenyl or pharmaceutically acceptable salt thereof.

2. The method of claim 1, wherein the deprenyl is (−) deprenyl.

3. The method of claim 1 wherein the patient is human.

4. The method of claim 1 wherein the patient is a non-human mammal.

5. The method of claim 1 wherein the patient has damaged nerve cells resulting from a neurodegenerative disease.

6. The method of claim 1 wherein the patient has damaged nerve cells resulting from a neuromuscular disease.

7. The method of claim 1 wherein the patient has damaged nerve cells resulting from hypoglycemia.

8. The method of claim 1 wherein the patient has damaged nerve cells resulting from a head trauma.

9. The method of claim 1 wherein the patient has damaged nerve cells resulting from Parkinson's disease.

10. The method of claim 1 wherein the patient has damaged nerve cells resulting from amyotrophic lateral sclerosis.

11. The method of claim 1 wherein the patient has damaged nerve cells resulting from spinal cord damage.

12. A method for rescuing damaged nerve cells in a patient, comprising:

topically administering to a patient in need thereof deprenyl, or a pharmaceutically acceptable salt thereof, such that rescuing of damaged nerve cells occurs in the patient in a condition in which the damaged nerve cells are sensitive to said deprenyl or pharmaceutically acceptable salt thereof.

13. The method of claim 12 wherein the deprenyl is (−)deprenyl.

14. A method for rescuing damaged nerve cells in a patient, comprising:

administering to a patient in need thereof deprenyl, or a pharmaceutically acceptable salt thereof, such that rescuing of damaged nerve cells occurs in the patient for a condition in which the damaged nerve cells are sensitive to said deprenyl or pharmaceutically acceptable salt thereof, wherein the deprenyl or pharmaceutically acceptable salt thereof is the only active ingredient administered.

15. The method of claim 14, wherein the deprenyl is (−)deprenyl.

16. The method of claim 14 wherein the patient is human.

17. The method of claim 14 wherein the patient is a non-human mammal.

* * * * *